(12) United States Patent
Sun et al.

(10) Patent No.: US 8,486,428 B2
(45) Date of Patent: Jul. 16, 2013

(54) COMPOSITIONS AND METHODS FOR MAKING AND USING ACYCLIC N-HALAMINE-BASED BIOCIDAL POLYMERIC MATERIALS AND ARTICLES

(75) Inventors: Yuyu Sun, Austin, TX (US); Jie Luo, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 720 days.

(21) Appl. No.: 11/389,968

(22) Filed: Mar. 27, 2006

(65) Prior Publication Data

US 2007/0224161 A1    Sep. 27, 2007

(51) Int. Cl.
*A01N 25/00* (2006.01)
*A61K 31/785* (2006.01)

(52) U.S. Cl.
USPC .......................... 424/405; 424/78.12

(58) Field of Classification Search
None
See application file for complete search history.

(56) References Cited

U.S. PATENT DOCUMENTS

| | | |
|---|---|---|
| 3,285,928 A | 11/1966 | Gubitz |
| 3,488,701 A | 1/1970 | Herbes et al. |
| 3,876,657 A | 4/1975 | Aelony et al. |
| 3,971,757 A | 7/1976 | Rasberger |
| 3,975,462 A | 8/1976 | Murayama et al. |
| 4,091,223 A | 5/1978 | Zussman et al. |
| 4,097,587 A | 6/1978 | Soma et al. |
| 4,241,208 A | 12/1980 | Murayama et al. |
| 4,785,055 A * | 11/1988 | Dexter et al. ............ 525/356 |
| 4,931,562 A | 6/1990 | Akabane et al. |
| 5,057,562 A | 10/1991 | Reinert |
| 5,459,145 A | 10/1995 | Saccomano et al. |
| 5,490,983 A | 2/1996 | Worley et al. |
| 5,580,872 A | 12/1996 | Chu et al. |
| 5,670,646 A | 9/1997 | Worley et al. |
| 5,705,545 A | 1/1998 | Avar et al. |
| 5,714,127 A | 2/1998 | DeWitt et al. |
| 5,817,806 A | 10/1998 | Rossi |
| 5,882,357 A | 3/1999 | Sun et al. |
| 5,889,130 A | 3/1999 | Worley et al. |
| 5,902,818 A | 5/1999 | Worley et al. |
| 6,020,491 A | 2/2000 | Wonley et al. |
| 6,077,319 A | 6/2000 | Sun et al. |
| 6,162,452 A | 12/2000 | Worley et al. |
| 6,241,783 B1 | 6/2001 | Sun et al. |
| 6,294,185 B1 | 9/2001 | Worley et al. |

(Continued)

FOREIGN PATENT DOCUMENTS

| | | |
|---|---|---|
| DE | 1900169 | 9/1969 |
| DE | 24 37 916 A | 2/1976 |

(Continued)

OTHER PUBLICATIONS

Hahn, Chlorination of Substituted Polyacrylamides, Die Angewandte Makromolekulare Chemie, 1976, 50, 53-65.*

(Continued)

*Primary Examiner* — Paul Dickinson
(74) *Attorney, Agent, or Firm* — Chainey P. Singleton; Edwin S. Flores; Chalker Flores, LLP

(57) ABSTRACT

The present invention includes methods and compositions for providing rechargeable aliphatic N-halamine polymers, monomers, copolymers additives and coatings. The rechargeable aliphatic N-halamine includes an aliphatic N-halamine compound exchangeable associated with one or more halides.

13 Claims, 12 Drawing Sheets

U.S. PATENT DOCUMENTS

| | | | |
|---|---|---|---|
| 6,409,941 B1 | 6/2002 | Galbo et al. | |
| 6,482,756 B2 | 11/2002 | Li | |
| 6,576,154 B1 | 6/2003 | Li | |
| 6,585,989 B2 | 7/2003 | Herbst et al. | |
| 6,670,412 B1 | 12/2003 | Erderly et al. | |
| 6,746,154 B2 | 6/2004 | Greene et al. | |
| 6,762,225 B2 | 7/2004 | Malik et al. | |
| 6,768,009 B1 | 7/2004 | Sun et al. | |
| 6,770,287 B1 | 8/2004 | Sun et al. | |
| 6,878,761 B2 | 4/2005 | Gugumus | |
| 6,969,769 B2 | 11/2005 | Worley et al. | |
| 7,084,208 B2 | 8/2006 | Sun et al. | |
| 7,335,373 B2 | 2/2008 | Worley et al. | |
| 7,541,398 B2 | 6/2009 | Sun et al. | |
| 8,211,361 B2 | 7/2012 | Sun et al. | |
| 2002/0123281 A1 | 9/2002 | Wu | |
| 2003/0056297 A1* | 3/2003 | Sun | 8/115.51 |
| 2003/0064645 A1 | 4/2003 | Worley et al. | |
| 2003/0143187 A1 | 7/2003 | Worley et al. | |
| 2004/0063831 A1 | 4/2004 | Sheppard et al. | |
| 2004/0086480 A1 | 5/2004 | Worley et al. | |
| 2004/0121681 A1 | 6/2004 | Quincy et al. | |
| 2004/0127667 A1 | 7/2004 | Worley et al. | |
| 2004/0191315 A1 | 9/2004 | Slattery et al. | |
| 2004/0265565 A1 | 12/2004 | Fischer et al. | |
| 2004/0266918 A1 | 12/2004 | Balliello et al. | |
| 2005/0186173 A1 | 8/2005 | Worley et al. | |
| 2006/0148940 A1 | 7/2006 | Sun et al. | |
| 2007/0062884 A1 | 3/2007 | Sun et al. | |
| 2007/0086976 A1 | 4/2007 | Sun et al. | |
| 2007/0092724 A1 | 4/2007 | Li et al. | |
| 2008/0268189 A1 | 10/2008 | Sun et al. | |
| 2009/0074825 A1 | 3/2009 | Sun et al. | |

FOREIGN PATENT DOCUMENTS

| | | |
|---|---|---|
| DE | 24 37 917 A | 2/1976 |
| EP | 02 40 370 A | 10/1987 |
| GB | 1211521 A | 11/1970 |
| WO | 94/20118 A1 | 9/1994 |
| WO | 96 08 949 A | 3/1996 |
| WO | 98/10648 A1 | 3/1998 |
| WO | 01/07550 A1 | 2/2001 |
| WO | 01/72715 A2 | 10/2001 |
| WO | 02/06479 A2 | 1/2002 |
| WO | 0206579 A2 | 1/2002 |
| WO | 0230477 A2 | 4/2002 |
| WO | 2005/058814 A2 | 6/2005 |
| WO | 2006074455 A2 | 7/2006 |
| WO | 2007126775 A2 | 11/2007 |
| WO | 2009039180 A2 | 3/2009 |

OTHER PUBLICATIONS

Translation of Hahn, Chlorination of Substituted Polyacrylamides, Die Angewandte Makromolekulare Chemie, 1976, 50, 53-65.*

Aggarwal, P., et al., "Development of an infection-resistant bifunctionalized Dacron biomateria," J Biomed Mater Res (2005), 75A:224-231.

Barker, J., et al., Effects of cleaning and disinfection in reducing the spread of Norovirus contamination via environmental surfaces, J Hosp Infect (2004), 58:42-49.

Braun, M., et al., "Antimicrobial Polymers Containing Melamine Derivatives. I. Preparation and Characterization of Chloromelamine-Based Cellulose," J Polym Sci Part A Polym Chem (2004), 42:3818-3827.

Cen, L., et al., "Antibacterial activity of cloth functionalized with Nalkylated poly(4-vinylpyridine)," J Biomed Mater Res (2004), 71A:70-80.

Chen, Z., et al., "N-Chloro-Hindered Amines as Multifunctional Polymer Additives," Macromolecules (2005), 38:8116-8119.

Larson, M. A., et al., "Inactivation of Bacillus subtilis spores with ozone and monochloramine," Water Research (2003), 37:833-844.

Lee, H. J., et al., "Antibacterial effect of nanosized silver colloidal solution on textile fabrics," J Mater Sci (2003), 38:2199-2204.

Lin, J., et al., "Antimicrobial Treatment of Nylon," J Appl Polym Sci (2001), 81:943-947.

Neely, A. N., et al. "Survival of Enterococci and Staphylococci on Hospital Fabrics and Plastic," J Clin Microbiol (2000), 38:724-726.

Neely, A. N., et al., "Survival of Some Medically Important Fungi on Hospital Fabrics and Plastics," J Clin Microbiol (2001), 39:3360-3361.

Sun, G., et al., "Durable and Regenerable Antibacterial Finishing of Fabrics with a New Hydantoin Derivative," Ind Eng Chem Res (2001), 40:1016-1021.

Sun, Y., et al., "Novel Refreshable N-Halamine Polymeric Biocides Containing Imidazolidin-4-one Derivatives," J Polym Sci Part A Polym Chem (2001), 39:3073-3084.

Sun, Y., et al., "Durable and Regenerable Antimicrobial Textile Materials Prepared by a Continuous Grafting Process," J Appl Polym Sci (2002), 84:1592-1599.

Sun, Y., et al., "Novel Refreshable N-Halamine Polymeric Biocides: N-Chlorination of Aromatic Polyamides," Ind Eng Chem Res (2004), 43:5015-5020.

Tennen, R., et al., "Mechanisms of killing of spores of Bacillus subtilis by iodine, glutaraldehyde and nitrous acid," J Appl Microbiol (2000), 89:330-338.

Albert, M., et al., "Structure-Activity Relationships of Oligoguanidines-Influence of Counterion, Diamine, and Average Molecular Weight on Biocidal Activies," Biomacromolecules, (2003), 4:1811-1817.

Amornsakchai, T., et al.,, "Surface modification of low density polyethylene using accelerated decomposition of potassium persulfate and ceric ion induced acrylamide grafting." J Mater Sci Lett (2002), 21:1035-1038.

Appendini, P., et al., "Review of antimicrobial food packaging," Innov. Food Sci. Emerg. Tech. (2002), 3:113-126.

Binder, S., et al., "Emerging Infectious Diseases: Public Health Issues for the 21st Century," Science (1999), 284:1311-1313.

Chen, C. Z., et al., "Quaternary Ammonium Functionalized Poly(propylene imine) Dendrimers as Effective Antimicrobials: Structure-Activity Studies," Biomacromolecules, (2000), 1:473-480.

Depaola, L.G., et al., "A review of the science regarding dental unit waterlines." J Am Dent Assoc (2002),133:1199-1206.

Dhamodharan, R., et al., "Investigation of the mercat reaction as a tool for the introduction of nitrogen surface functionality on linear low-density polyethylene (LLDPE) and polypropylene (PP)." Langmuir (2001),17:3368-3374.

Eknoian, M. W., et al., "Monomeric and Polymeric N-Halamine Disinfectants," Ind. Eng. Chem. Res. (1998), 37:2873-2877.

Eknoian, M. W., et al., "Novel Antimicrobial N-halamine polymer coatings generated by emulsion polymerization," Polymer (1999), 40:1367-1371.

Gorman, S.P., et al., "The concomitant development of poly(vinyl chloride)-related biofilm and antimicrobial resistance in relation to ventilator-associated pneumonia." Biomaterials (2001),22:2741-2747.

Hall-Stoodley, L., et al., "Bacterial biofilms: from the natural environment to infectious diseases." Nature Rev Microbiol (2004),2:95-108.

Jansson, A., et al., "Degradation of post-consumer polypropylene materials exposed to simulated recycling—mechanical properties," Polym. Degrad. Stab. (2003), 82:37-46.

Kruczala, K., et al., "Thermal Aging of Heterophasic Propylene-Ethylene Copolymers: Morphological Aspects Based on ESR, FTIR, and DSC," Macromolecules (2003), 36:1899-1908.

Kruczala, K., et al., "Thermal Aging of Heterophasic Propylene-Ethylene Copolymers: Spatial and Temporal Aspects of Degradation Based on ESR, ESR Imaging, and FTIR," Macromolecules (2003), 36:1909-1919.

Lee, S. B., et al., "Permanent, Nonleaching Antibacterial Surfaces. 1. Synthesis by Atom Transfer Radical Polymerization," Biomacromolecules, (2004), 5:877-882.

Lin, J., et al., "Infrared characterization of biocidal nylon." Polymer (2001), 42:7903-7906.

Linger J.B., et al., "Evaluation of a hydrogen peroxide disinfectant for dental unit waterlines." J Am Dent Assoc (2001),132:1287-1291.

Luo J., et al., "Acyclic N-halamine-based fibrous materials: preparation, characterization, and biocidal functions." J Polym Sci: Part A Polym Chem (2006),44:3588-3600.

Mills S.E., "The dental unit waterline controversy: defusing the myths, defining the solutions." J Am Dent Assoc (2000),131:1427-1441.

Motyakin, M. V., et al., "Spectral Profiling by 1D and 2D Electron Spin Resonance Imaging: Nitroxide Radicals in UV and Thermal Degradation of Poly(acrylonitrile-butadiene-styrene) Containing a Hindered Amine Stabilizer," Macromolecules (2001), 34:2854-2864.

Motyakin, M. V., et al., "Electron Spin Resonance Imaging and ATR-FTIR Study of Poly(acrylonitrile-butadiene-styrene) Containing a Hindered Amine Stabilizer and Thermally Treated at 353 K," Macromolecules (2002), 35:3984-3992.

Muzzarelli, R. A. A., et al., "Fungistatic Activity of Modified Chitosans against *Saprolegnia parasitica*," Biomacromolecules, (2001); 2:165-169.

Ozcan M., et al., "The effect of disinfectant agents in eliminating the contamination of dental unit water." J Oral Rehabili (2003),30:290-294.

Qian, L., et al., "Durable and Regenerable Antimicrobial Textiles: Improving Efficacy and Durability of Biocidal Functions," J Appl Polym Sci (2004), 91:2588-2593.

Rabea, E. I., et al., "Chitosan as Antimicrobial Agent: Applications and Mode of Action," Biomacromolecules, (2003), 4:1457-1465.

Ramage G., et al., "Formation of Propionibacterium acnes biofilms on orthopaedic biomaterials and their susceptibility to antimicrobials." Biomaterials (2003),24:3221-3227.

Roberts H.W., et al., "Dental unit waterline antimicrobial agent: effect on dentin bond strength." J Am Dent Assoc (2000),131:179-183.

Setnescu, R., et al., "Chemiluminescence study on the oxidation of several polyolefins-I. Thermal-induced degradation of additive-free polyolefins," Polym. Degrad. Stab. (1998), 60:377-383.

Sun, G., et al., National Center Annual Report, NTC Project CO2-CD06 (Nov. 2002).

Sun, Y., et al., "Synthesis, Characterization, and Antibacterial Activities of Novel N-Halamine Polymer Beads Prepared by Suspension Copolymerization," Macromolecules (2002), 35:8909-8912.

Sun, Y. et al. "Novel Refreshable N-Halamine Polymeric Biocides: Grafting Hydantoin-Containing Monomers onto High Performance Fibers by a Continuous Process," J. Appl. Polym. Sci. (2003), 88:1032-1039.

Tao G., et al., "Surface functionalized polypropylene: Synthesis, characterization, and adhesion properties." Macromolecules (2001),34:7672-7679.

Tew, G. N., et al., "De novo design of biomimetic antimicrobial polymers," Proc. Natl. Acad. Sci. USA. (2002), 99:5110-5114.

Tiller, J. C., et al., "Designing Surfaces that Kill Bacteria on Contact," Proc. Natl. Acad. Sci. USA. (2001), 98:5981-5985.

Walker J.T., et al., "Microbiological evaluation of a range of disinfectant products to control mixed-species biofilm contamination in a laboratory model of a dental unit water system." Appl Environ Microbiol (2003),69:3327-3332.

Yorganci K., et al., "Activity of antibacterial impregnated central venous catheters against *Klebsiella pneumoniae*." Intensive Care Med (2002),28:438-442.

International Search Report and Written Opinion for PCT/US2008/076687 dated Apr. 3, 2009.

International Search Report and Written Opinion for PCT/US2007/007506 dated Jul. 25, 2008.

Nishimoto, et al., "Radiation-induced structural changes in poly (propylene-ran-ethylene) film: effect of antioxidant 2,2,6,6-tetramethylpiperidine derivatives," Radiat. Phys. Chem. (1992), 39(5):413-419.

International Search Report and Written Opinion for PCT/US2001/09071 dated Jul. 18, 2002.

International Search Report and Written Opinion for PCT/US2006/00849 dated Jul. 18, 2002.

Worley, et al. "A Novel N-Halamine Monomer for Preparing Biocidal Polyurethane Coatings" Air Force Research Laboratory, Mar. 31, 2002.

Bamford, et al. "Studies in polymer surface functionalization and grafting for biomedical and other applications" Polymer 1994, 35, 2844-2852.

Bloomfield, et al. "Effect of chlorine-releasing agents on *Bacillus subtilis* vegatative cells and spores" Lett. Appl. Microbiol. 1989, 8, 101-104.

Dart, et al. "Retention of *Aspergillus Niger* Spores on Textiles" ASTM Special Technical Publication 2000, STP 1386 (7), 251-268.

Datta, et al. "An Outbreak of infection with *Salmonella typhimuium* in a general hospital" J. Hyg. Camb. 1960, 58, 229-214.

Dixon, et al. "Quantitative Studies on Fabrics as Disseminators of Viruses" Appl. Microbiol. 1966, 14, No. 2, 183-188.

George, et al. "Poly(N-bromoacrylamide): A New Polymeric Recyclable Oxidizing and Brominating Reagent" Macromolecules 1988, 21, 1867-1870.

Haas, et al. "Imidization Reaction in Polyvinylamides" J. Polym. Sci. Part A Polym. Chem. 1971, 9, 3583-3593.

Hardy, et al. "The Formation and Hydrolysis of Substituted N-Chloro-N-methylbenzamides in Aqueous Alkali", P. J. Chem. Soc. B. 1967, 1151-1154.

Lister, Joseph "On the Antiseptic Principle in the Practice of Surgery" Lancet 1867, 2, 353.

Neely, Alice N. "A Survey of Gram-Negative Bacteria Survival on Hospital Fabrics and Plastics" J. Burn. Care. Rehabil. 2000, 21, 523-527.

Oliphant, et al. "Fever in Laundry Workers, Presumable Transmitted From Contaminated Clothing" R. R. Am. J. Hyg. 1949, 47, 76-82.

Orr, et al. "Therapeutic beds: the Trojan horses of the 1990s?" Lancet 1994, 344, 65-66.

Phaneuf, et al. "Application of the quinolone antibiotic ciprofloxacin to Dacron utilizing textile dyeing technology". J. Biomed. Mater. Res. 1993, 27, 233-237.

Richmond, et al. "Biosafety in Microbiological and Biomedical Laboratories" 4th ed.; U.S. Government printing office: Washington, DC, Apr. 1999 (265 pp.).

Sidwell, et al. "Quantitative Studies on Fabrics as Disseminators of Viruses—I. Persistence of Vaccinia Virus on Cotton and Wool Fabrics" Appl. Microbiol. 1966, 14, 55-59.

Sidwell, et al. Quantitative Studies on Fabrics as Disseminators of Viruses—III. Persistence of Vaccinia Virus on Fabrics Impregnated with a Virucidal Agent Appl. Microbiol. 1967, 15, 921-927.

Sidwell, et al. Quantitative Studies on Fabrics as Disseminators of Viruses—IV. Virus Transmission by Dry Contact of Fabrics Appl. Microbiol. 1970, 19, 950.

Sidwell, et al. "Quantitative Studies on Fabrics as Disseminators of Viruses—V. Effect of Laundering on Poliovirus-Contaminated Fabrics" Appl. Microbiol. 1971, 21, 227-234.

Standaert, et al. "Nosocomial Transmission of *Salmonella Gastroenteritis* to Laundry Workers in a Nursing Home" Infect. Control Hosp. Epidemiol. 1994, 15, 22-26.

Suffis, et al. "Spectrophotometric Determination of a p-Phenylenedia-mines and p-Aminophenols with Nihndrin" Analytical Chemistry, vol. 36, No. 3, Mar. 1964, pp. 636-637.

Sykes, G. "The Sporicidal Properties of Chemical Disinfectants" J. Appl. Bact. 1970, 33, 147-156.

\* cited by examiner

US 8,486,428 B2

COMPOSITIONS AND METHODS FOR MAKING AND USING ACYCLIC N-HALAMINE-BASED BIOCIDAL POLYMERIC MATERIALS AND ARTICLES

CROSS-REFERENCE TO RELATED APPLICATIONS

This application is related to U.S. Provisional Patent Application Ser. No. 60/707,331, filed Aug. 11, 2005, U.S. patent application Ser. No. 11/324,616, filed Jan. 3, 2006, and to U.S. Provisional Patent Application Ser. No. 60/640,985, filed Jan. 3, 2005, the contents of each of which are incorporated by reference herein in their entireties.

TECHNICAL FIELD OF THE INVENTION

The present invention relates in general to the field of biocidal polymers and more particularly, to compositions and methods to make and use rechargeable acyclic N-halamine based biocidal polymers or articles.

BACKGROUND OF THE INVENTION

Without limiting the scope of the invention, its background is described in connection with polymeric biocides. To contain the spread of infectious pathogens, materials that can effectively inactivate microorganisms upon contact have attracted considerable interest. One common method in the preparation of antimicrobial materials is to directly add antimicrobial additives into materials during processing.

Many materials (e.g., polymers, fibers, medical devices prone to biofilms) are remarkably difficult to treat with antimicrobials, which may be readily inactivated or fail to penetrate into the materials. In addition, bacteria within such materials have increased resistance to antimicrobial compounds, even though these same bacteria are sensitive to these agents if grown under planktonic conditions. Furthermore, bacteria express new, and sometimes more virulent phenotypes when grown within different materials. The growth conditions are quite different particularly in the depths of biofilms, where nutrients and oxygen are usually limited, and waste products from neighbors can be toxic. In short, bacteria found at the bottom of the materials can look and act different from bacteria located at the surface. The medical, industrial and environmental fields already see such problems, e.g., bacteria resistant to both immunological and non-specific defense mechanisms of the body.

Microorganisms have strong abilities to survive on ordinary materials and studies have shown that some species can stay alive for as long as 90 days. The contaminated materials serve as major sources of infectious diseases. Therefore, the introduction of biocidal functions into a target material can be an effective method to inactivate the microbes and thus reduce infection rates. Although many technologies have attempted this process, successful examples in this field are still limited.

U.S. Pat. No. 6,762,225, issued to Malik, et al., for light stabilizer composition and teaches a light stabilizer composition obtainable by mixing a polymer with at least one polyalkylpiperidine and at least one free radical generator and melt-blending of that mixture at a temperature above the melting point of the polymer and above the decomposition temperature of the free radical generator and at shear conditions sufficient to blend the components. The light stabilizers of this patent provide a method for enhancing the light stability of polymers, preferably polyolefins.

U.S. Pat. No. 6,670,412, issued to Erderly, et al., for a method of melt processing amine containing polyethylenes and teaches a processed linear polyethylene containing an amine additive shown to exhibit improved processability through the addition of certain surfactants. The amine compounds are generally one or more hindered amine light stabilizers, amine antistats, amine antioxidants or amine based UV inhibitors. Among the melt processing parameters improved are reduced head pressure, reduced torque, reduced motor load, reduced or eliminated melt fracture, or combinations of these parameters.

The foregoing problems have been recognized for many years and while numerous solutions have been proposed, none of them adequately addresses all of the problems.

SUMMARY OF THE INVENTION

The present inventors recognized a need for a simple and practical, yet flexible and cost-effective method to transform a wide range of materials into durable and rechargeable biocidal materials. The present inventors recognized that a self decontamination composition was needed and had wide applications, e.g., medical devices, hospital equipment, water purification/delivery systems, food storage and food packaging, hygienic products, bioprotective applications and other related challenging environments.

The present invention provides biocidal materials that can inactivate bacteria, spores, fungi, yeasts, and virus. The present invention uses acyclic N-halamine materials to provide biocidal functions. Generally an N-halamine is a compound containing one or more nitrogen-halogen covalent bonds that is normally formed by the chlorination or bromination of imide, amide or amine groups of a compound. One property of N-halamines is that when microbes come into contact with the N—X structures (X is Cl or Br), a halogen exchange reaction occurs, resulting in the expiration of the microorganisms. This process consumes halogens, but the consumed halogens can be fully recharged by another halogen treatment. Thus, N-halamines are generally regarded as rechargeable batteries of covalently bound halogens. Currently, the majority of N-halamine antimicrobial materials contain cyclic structures to ensure the stability of the nitrogen-halogen covalent bond. However, polymerizable cyclic N-halamines or their precursors are not commercially available, and they are expensive to produce for large quantity applications.

More particularly, a method and composition are provided that include a class of acyclic biocidal materials, e.g., methacrylamide (MAA)-based. MAA is polymerized to form its homopolymer, polymethacrylamide (PMAA), MAA is copolymerized with other polymerizable monomers to form copolymers or MAA is grafted onto other polymeric materials with or without the presence of other monomers to form grafted copolymers. The resultant MAA-based polymers can be used alone, blended/mixed with other materials, or coated/painted onto other materials. Upon exposure to a halogen source(s), acyclic N-halamines are formed in the MAA-based materials, which can provide durable and rechargeable biocidal effects against bacteria, spores, fungi, yeasts and virus.

The N-halamine compounds of the present invention include acyclic compounds. The acyclic N-halamine compounds of the present invention include aliphatic compounds that are non-aromatic organic compounds and have a general open chain hydrocarbon structure, e.g., not only fatty acids and other derivatives of the paraffin hydrocarbons (alkane), but also unsaturated compounds, such as the ethylene (alkene) and acetylene (alkyne) series. The number of molecules in the chain may vary depending on the application and the compound may be branched or unbranched. In addition, compounds may contain modifications, side groups, substitutions, additions and other modifications that are known to the skilled artisan.

For example, methacrylamide (MAA) (2-methylprop-2-enamide) was grafted onto cotton cellulose. The influences of reaction conditions on grafting were studied in details. Upon chlorine bleach treatment, some of the amide groups in the grafted MAA side chains were transformed into stable acyclic N-halamines. The resultant cotton celluloses provided a total kill of about $10^8$-$10^9$ colony forming units/mL of $E.$ $coli$ (gram-negative bacteria), $S.$ $aureus$ (gram-positive bacteria), and $C.$ $tropicalis$ (fungi) in 3 minutes, $10^6$-$10^7$ plaque forming units/mL of MS2 virus in 5 minutes, and $10^6$-$10^7$ spores/mL of $Bacillus$ $subtilis$ spores in 4 hours. The antibacterial, antifungal, antiviral, and anti-spore activities were both durable and rechargeable.

The present invention includes a rechargeable acyclic N-halamine polymer. The rechargeable acyclic N-halamine polymer includes one or more acyclic N-halamine monomers and one or more halides associated with one or more acyclic N-halamine monomers. The one or more halides provided inactivation of bacteria cells, spores, fungus, yeasts, viruses or a combination thereof.

The present invention also provides a rechargeable biocidal organic polymer. The rechargeable biocidal organic polymer is made by polymerizing one or more aliphatic N-halamine monomers and contacting the one or more aliphatic N-halamine monomers with a halide source to form an activated aliphatic acyclic N-halamine organic polymer. The activated aliphatic N-halamine organic polymer has biocidal activity against bacteria, spores, fungi, yeasts, virus or a combination thereof.

A rechargeable biocidal fabric is also provided by the present invention. The rechargeable biocidal fabric is made by forming an acyclic N-halamine polymer having one or more acyclic N-halamine monomers and forming an acyclic N-halamine fabric from the acyclic N-halamine polymer. Articles and garments can be constructed from the acyclic N-halamine fabric. The acyclic N-halamine fabric is contacted with a halide source to activate the biocidal activity against bacteria, spores, fungi, yeasts, virus or a combination thereof.

One embodiment of the present invention provides a rechargeable methacrylamide cotton fabric having antimicrobial activity. The rechargeable methacrylamide cotton fabric includes a methacrylamide compound grafted to a cotton cellulose and one or more halides associated with the methacrylamide compound to produce antimicrobial activity against bacteria, spores, fungi, yeasts, virus or a combination thereof.

A method is also provided for making a biocidal polymer by polymerizing one or more acyclic N-halamine monomers into a polymer and contacting the one or more acyclic N-halamine monomers with a halide source to form an activated acyclic N-halamine polymer with biocidal activity against bacteria, spores, fungi, yeasts, virus or a combination thereof.

In addition, the present invention provides for the production of polymers, polymer additives, copolymers, coatings, and the like that produce biocidal activity against bacteria, spores, fungi, yeasts, virus or a combination thereof. The polymers, polymer additives, copolymers, coatings and the like contain one or more aliphatic N-halamine monomers polymerized into a polymer and one or more halides exchangeable associated with the one or more aliphatic N-halamine monomers to produce biocidal activity against bacteria, spores, fungi, yeasts, virus or a combination thereof. The one or more aliphatic N-halamine monomers impart the polymers, polymer additives, copolymers, coatings and the like with a rechargeable biocidal activity against bacteria, spores, fungi, yeasts, virus or a combination thereof.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
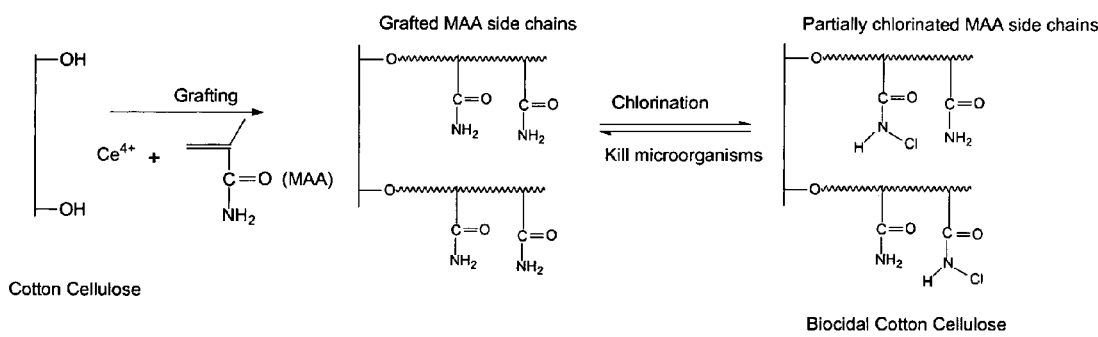
FIG. 1 is a schematic that illustrates the preparation of biocidal cotton cellulose.

While the making and using of various embodiments of the present invention are discussed in detail below, it should be appreciated that the present invention provides many applicable inventive concepts that can be embodied in a wide variety of specific contexts. The terminology used and specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention provides a polymerizable acyclic N-halamine precursor to form homopolymer or heteropolymers including segmented polymers, block polymers, multi-block polymers, gradient polymers, graft polymers, star polymers, branched polymers, hyperbranched polymer and combinations thereof. The acyclic N-halamine polymers can be used alone, or they can be blended/mixed with other materials or coated/painted onto other materials. After exposure to a halogen source(s), the resultant materials show biocidal activity against bacteria, spores, fungi, yeasts, and virus. Furthermore, upon the loss of biocidal activity due to extensive use, the activity can be easily recharged.

For example, methacrylamide is grafted onto cotton cellulose using cerium (IV) ammonium nitrate as initiators. The skilled artisan will recognize that other initiators may be used. Upon chlorine bleach treatment, some of the amide groups of the grafted methacrylamide side chains are transformed into stable acyclic N-halamines. The active chlorine content of the fabrics increases with the increase of percentage graft yield until a saturated value is reached. The chlorination reaction is markedly enhanced by weak acidic conditions. The chlorinated MAA-grafted samples provide potent, durable and rechargeable antibacterial, antifungal, antiviral, and, for the first time, anti-spore functions in the vegetative and non-vegetative states. In addition to antibacterial, antifungal, antiviral the present invention provides anti-fungal and anti-odor functions. The new cotton celluloses may find wide applications as infection-resistant hospital, medical, and bio-protective fibrous materials As used herein the term "alkyl," by itself or as part of another substituent, means, unless otherwise stated, a straight or branched chain, or cyclic hydrocarbon radical, or combination thereof, which may be fully saturated, mono- or poly-unsaturated and can include di-valent and multivalent radicals, having the number of carbon atoms designated.

As used herein the term "alkylene" by itself or as part of another substituent means a divalent radical derived from an alkane and further includes those groups known as "heteroalkylenes."

As used herein the terms "alkoxy," "alkylamino," "alkylthio" and "thioalkoxy" are used in their conventional sense, and refer to those alkyl groups attached to the remainder of the molecule via an oxygen atom, an amino group or a sulfur atom, respectively.

As used herein the term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. Still further, for alkylene and heteroalkylene linking groups, no orientation of the linking group is implied.

As used herein the terms "halo" or "halogen," by themselves or as part of another substituent, mean, unless otherwise stated, chlorine, bromine or iodine atom. Additionally, terms such as "haloalkyl" are meant to include monohaloalkyl and polyhaloalkyl.

As used herein the term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

Substituents for the alkyl and acyl, e.g., those groups often referred to as alkylene, alkenyl, heteroalkylene, heteroalkenyl, alkynyl, cycloalkyl, heterocycloalkyl, cycloalkenyl, and heterocycloalkenyl.

The terms "antimicrobial compound," "antimicrobial," "microbicidal," "biocide," "biocidal" "antiodor" and "halogenated amide antimicrobial" are used interchangeably herein and refer to halogenated amides that function as biocides to kill at least some types of microorganisms, or to inhibit the growth or reproduction of at least some types of microorganisms, i.e., compounds which inhibit the growth of, or kills, microorganisms such as bacteria, molds, slimes, fungi, etc. As a result of inhibiting the growth or killing of organisms the odor can be eliminated.

As used herein, the terms, "polymer" and "copolymer" are at times used interchangeably to mean an amine or N-halamine unit joined by a linkage to a second amine or N-halamine unit is not meant to be limiting as to the number of amine or N-halamine units in a polymer, e.g., two or more amine or N-halamine units, and the number of units in any given polymer can vary according to the use intended for the polymer. For example, the polymer can include 2, 3, 4, 5, 6, 7, 8, 9, 10, 20, 25, 30, 40, 50, 75, 100, 150, 200, 250, 500, 1000, and so forth, units.

Olefins as used herein include any compound that has only one double bond $C=C$, and consists only of C and H. Halo-olefins as used herein include any compound that has only one double bond $C=C$, and doesn't contain elements other than C, H, and halogen (X), where X is F, Cl, Br or I. Dienes as used herein include any compound that has two double bonds $C=C$ or more. Acetylenes as used herein include any compound that has one triple bond $C\equiv C$ or more. When monomer has the structure of $C\equiv C-R$, it is classified into here regardless of the structure of R. Styrenes as used herein include any compound that has structure of $C=C-Ar$, where Ar is an aromatic series is ring. Acrylic acids (acrylics) as used herein include any compound that has $C=C-CO-Z$ (where $Z=O$ or S or N) or $C=C-CN$ structure. Vinyl compounds as used herein include any compound that has vinyl group $C=C-$, and has atom or aromatic rings other than C and H. Halo-olefins, Styrenes, and acrylics may also be classified into Vinyl compounds.

The present invention includes a rechargeable acyclic N-halamine polymer. The rechargeable acyclic N-halamine polymer includes one or more acyclic N-halamine monomers and one or more halides associated with the one or more acyclic N-halamine monomers. The one or more halides provided inactivation of bacteria cells, spores, fungus, yeasts, viruses or a combination thereof.

In one example, the acyclic N-halamine polymer is a methacrylamide polymer; however, other monomers may be used to form the acyclic N-halamine polymer of different compositions. In addition, the acyclic N-halamine polymer may be constructed from a variety of monomers of similar or different types and combinations to produce a polymeric material. In addition, the present invention may be used as an additive in paints, coatings, cleaners, topical solutions and gels, foams and so forth to provide antimicrobial, antimicrobial, biocidal and antiodor functions to kill at least some types of microorganisms, or to inhibit the growth or reproduction of at least some types of microorganisms.

The N-halamine polymer may be made up of one type of monomer (e.g., homopolymers) or two or more different type monomers are involved, the resulting heteropolymer or copolymer can have several configurations or arrangements of the monomers along the chain. For example the random copolymer has different types of monomer randomly distributed throughout the polymer chain(s), the alternating copolymer has different types of monomer distributed in an alternating manner throughout the polymer chain. The block copolymer has different types of monomer arranged in groups of similar monomers along the polymer chain, while graft copolymers have branches of one monomer or another extending from the polymer chain. The polymers of the present invention may be homopolymers or heteropolymer and include random polymers, block polymers, graft polymers or segments and combinations thereof.

The aliphatic or acyclic N-halamine monomer is polymerized and grafted to another polymer, e.g., cellulose or cotton. Some embodiments of the rechargeable acyclic N-halamine polymer are formed into fibers or fabrics. This allows the formation of garments, articles, surgical fabrics, surgical garments, masks and apparel, which has numerous applications from clothes to bed and seat covers to masks and surgical supplies.

In addition, the present invention is rechargeable by contacting the aliphatic or acyclic N-halamine grafted polymer with a halide source to recharge the aliphatic or acyclic N-halamine monomer. Thus once the aliphatic or acyclic N-halamine polymer has lost at least part of the microbial activity it can be replaced or recharged to again inactivate bacteria cells, spores, fungus, yeasts, viruses or a combination thereof.

Thus once the aliphatic or acyclic N-halamine polymer has lost at least part of the microbial activity it can be replaced or recharged to again inactivate bacteria cells, spores, fungus, yeasts, viruses or a combination thereof. Some examples of recharging halide sources include hypochlorite solution, sodium di-X-isocyanurate, sodium hypohalite, N—X-succinimide, and calcium hypohalite, wherein X is selected from Cl or Br.

The present invention also provides a rechargeable biocidal organic oligmer. The rechargeable biocidal organic oligmer is made by polymerizing one or more acyclic N-halamine monomers into an organic oligmer and contacting the one or more acyclic N-halamine monomers with a halide source to form an activated acyclic N-halamine organic oligmer. The activated acyclic N-halamine organic oligmer has biocidal activity against bacteria, spores, fungi, yeasts, virus or a combination thereof.

A rechargeable biocidal fabric is also provided by the present invention. The rechargeable biocidal fabric is made by polymerizing one or more acyclic N-halamine monomers into a polymer to form an acyclic N-halamine fiber. An acyclic N-halamine fabric is formed from the acyclic N-halamine fiber from which articles and garments can be constructed from the acyclic N-halamine grafted fabric. The acyclic N-halamine fabric is contacted with a halide source to activate the biocidal activity against bacteria, spores, fungi, yeasts, virus or a combination thereof.

One embodiment of the present invention provides a rechargeable methacrylamide cotton fabric having antimicrobial activity. The rechargeable methacrylamide cotton fabric includes one or more methacrylamide monomers grafted to a cotton cellulose and one or more halides associated with the one or more methacrylamide monomers to produce antimicrobial activity against bacteria, spores, fungi, yeasts, virus or a combination thereof.

A method is also provided for making a biocidal polymer by polymerizing one or more acyclic N-halamine monomers and contacting the one or more acyclic N-halamine monomers with a halide source to form an activate acyclic N-halamine polymer with to biocidal activity against bacteria, spores, fungi, yeasts, virus or a combination thereof.

For example, the present invention provides a method of making a biocidal polymer by polymerizing one or more acyclic N-halamine monomers into random polymers, segmented polymers, block polymers, multiblock polymers, gradient polymers, graft polymers, star polymers, branched polymers, hyperbranched polymers or segments and combinations thereof.

The N-halamine polymer may be made up of one type of monomer (e.g., homopolymers) or two or more different type monomers are involved, the resulting heteropolymer or copolymer can have several configurations or arrangements of the monomers along the chain. For example, the random copolymer has different types of monomer randomly distributed throughout the polymer chain, the alternating copolymer has different types of monomer distributed in an alternating manner throughout the polymer chain. The block copolymer has different types of monomer arranged in groups of similar monomers along the polymer chain, while graft copolymers have branches of one monomer or another extending from the polymer chain. The polymer of the present invention may be homopolymers or heteropolymer and include random polymers, block polymers, graft polymers or segments and combinations thereof.

The aliphatic N-halamine precursor of monomers have the general formula of:

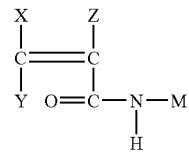

X, Y, Z or M can independently be alkyl groups, alkylene groups, alkenyl groups, alkynyl groups, aryl groups, alkoxy groups, alkylcarbonyl groups, alkylcarboxyl groups, amido groups, carboxyl groups, 4-8 membered ring groups, halogens, hydrogens or combinations thereof.

Typical examples of this formula include, but not limit to: acrylamide, methacrylamide, ethacrylamide, N-methylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[1,2-(dimethylamino)dodecyl]methacrylamide, N-[3-(diethylamino)propyl]methacrylamide, N-[3-(diethylamino)propyl]acrylamide; and combinations thereof.

The acyclic N-halamine compound is constructed from a variety of monomers of similar or different types and combinations to produce a polymeric material. One example is a methacrylamide polymer; however, other polymers may be used to form the acyclic N-halamine compound and other modification, substitutions, alterations and the like may be made to the acyclic N-halamine compound.

In one embodiment, the aliphatic N-halamine polymer is grafted to a grafting polymer. One example of a grafting polymer is cotton cellulose or other forms of cellulose, including bacterial cellulose. In addition the subunits may be altered, substituted or modified by the skilled artisan to produce specific characteristics in the polymer. Some embodiments of the rechargeable acyclic N-halamine grafted polymer are in the form of a polymer that can be formed into fibers or fabrics. This allows the formation of garments, articles, surgical fabrics, surgical garments, masks and apparel. This has numerous applications from clothes to bed and seat covers to masks and surgical supplies.

In addition, the present invention is rechargeable by contacting the activated acyclic N-halamine polymer with a halide source to recharge the activated acyclic N-halamine polymer. Thus once the activate acyclic N-halamine polymer has lost at least part of the microbial activity it can be replaced or recharged to again be inactivate bacteria cells, spores, fungus, yeasts, viruses or a combination thereof. Some examples of recharging halide sources include hypochlorite solution, sodium di-X-isocyanurate, sodium hypohalite, N—X-succinimide, and calcium hypohalite, wherein X is selected from Cl or Br.

In addition, the present invention provides for the production of polymers, polymer additives, copolymers, coatings, and the like that produce biocidal activity against bacteria, spores, fungi, yeasts, virus or a combination thereof. The polymers, polymer additives, copolymers, coatings, and the like contain one or more aliphatic N-halamine monomers polymerized into a polymer and one or more halides exchangeable associated with the one or more aliphatic N-halamine monomers to produce biocidal activity against bacteria, spores, fungi, yeasts, virus or a combination thereof. The one or more aliphatic N-halamine monomers imparts the polymers, polymer additives, copolymers, coatings, and the like with a rechargeable biocidal activity against bacteria, spores, fungi, yeasts, virus or a combination thereof.

Some of the modifications to the acyclic N-halamine, the aliphatic N-halamine compound, the N-halamine, the polymer, the individual monomers, the oligomers and other components of the present invention include the addition, deletion, substitution, or modification of one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

The N-halamine polymers of the present invention may be formed from a variety of monomers, e.g., olefins, dienes, acetylenes, styrenes, vinyl compounds and acrylic acids (acrylics) just to name a few. For example specific monomers used in the present invention include 1-vinylimidazole, butanediol divinyl ether, cyclohexane dimethanol divinyl ether, cyclohexane dimethanol monovinyl ether, cyclohexyl vinyl ether, diethyleneglycol divinyl ether, hydroxybutyl vinyl ether, octadecyl vinyl ether, tertiary butyl vinyl ether, triethyleneglycol divinyl ether, dimethylaminopropyl methacrylamide (DMAPMA) and combinations and modifications thereof.

For example the present invention may include monomers that have an N-halamine group or the monomers that are modified to include an N-halamine group. Some monomers used with the present invention include: dienes, such as butadiene, isoprene, myrcene, pentadienes, and furthermore $C_1$ to $C_{50}$ alkyl and hydroxyalkyl esters of monoethylenically unsaturated $C_3$ to $C_{50}$ monocarboxylic acids or dicarboxylic acids, for example methyl methacrylate, ethyl methacrylate, propyl methacrylate, butyl methacrylate, 2-ethylhexyl methacrylate, isobornyl methacrylate, methyl acrylate, ethyl acrylate, propyl acrylate, butyl acrylate, 2-ethylhexyl acrylate, isobornyl acrylate, benzyl acrylate, phenyl acrylate, stearyl acrylate, diethyl maleate, hydroxyethyl acrylate, hydroxypropyl acrylate, hydroxybutyl acrylate, benzyl methacrylate, phenyl methacrylate, stearyl methacrylate, methacrylonitrile, styrene, α-methylstyrene, acrylonitrile, functionalized methacrylates; acrylates and styrenes selected from glycidyl methacrylate, 2-hydroxyethyl methacrylate, hydroxypropyl methacrylate, hydroxybutyl methacrylate, cyclohexyl methacrylate, cyclohexyl acrylate, hexyl methacrylate and hexyl acrylate, diethylaminoethyl methacrylate, triethylene glycol methacrylate, itaconic anhydride, itaconic acid, glycidyl acrylate, 2-hydroxyethyl methacrylate, diethylaminoethyl acrylate, triethylene glycol acrylate, methacrylamide, N-tert-butylmethacrylamide, N-n-butylmethacrylamide, N-methylolmethacrylamide, N-ethylolmethacrylamide, N-tert-butylacrylamide, N-butylacrylamide, N-methylolacrylamide, N-ethylolacrylamide, vinylbenzoic acid, diethylaminostyrene, α-methylvinylbenzoic acid, diethylamino-α-methylstyrene, p-methylstyrene, p-vinylbenzenesulfonic acid, trimethoxysilylpropyl methacrylate, triethoxysilylpropyl methacrylate, tributoxysilylpropyl methacrylate, triethoxy-methylsilyipropyl methacrylate, dibutoxymethylsilylpropyl methacrylate, diisopropoxynethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate and vinyl butyrate, vinyl chloride, vinyl fluoride, vinyl bromide, vinyl alcohol, vinyl ethers of, vinyl ethers and vinyl ethers of polyalkylene oxides, such as polyethylene oxide, polypropylene oxide or polybutylene oxide, monoethylenically unsaturated monocarboxylic acids, acrylic acid, methacrylic acid, dimethylacrylic acid, ethylacrylic acid, allylacelic acid or vinylacetic acid, furthermore monoethylenically unsaturated dicarboxylic acids and isomers thereof.

The present invention also includes monomers containing amides and N-substituted amides of monoethylenically unsaturated $C_3$ to $C_{50}$-monocarboxylic acids or $C_3$ to $C_{50}$-dicarboxylic acids, for example acrylamide, N-alkylacrylamides or N,N-dialkylacrylamides, each having 1 to 50 carbon atoms in the alkyl group, such as N-methylacrylamide, N,N-dimethylacrylamide, N-tert-butylacrylamide or N-octadecylacrylamide, N-monomethylhexylmaleamide, N-monodecylmaleamide, diethylaminopropylmethacrylamide or acrylamidoglycollic acid; furthermore alkylaminoalkyl (meth)acrylates, for example dimethylaminoethyl acrylate, dimethylaminoethyl methacrylate, ethylaminoethyl acrylate, diethylaminoethyl methacrylate, dimethylaminopropyl acrylate or dimethylaminopropyl methacrylate.

Furthermore, the present invention includes monomers containing vinyl esters, such as vinyl formate, vinyl acetate or vinyl propionate, where these may also be present in hydrolyzed form after the polymerization; furthermore N-vinyl compounds, for example N-vinylpyrrolidone, N-vinylcaprolactam, N-vinylformamide, N-vinyl-N-methylformamide, 1-vinyl-imidazole or 1-vinyl-2-methylimidazole; furthermore vinyl ethers of $C_1$ to $C_{50}$ alcohols, vinyl ethers of alkoxylated $C_1$ to $C_{50}$ alcohols and vinyl ethers of polyalkylene oxides, such as polyethylene oxide, polypropylene oxide or polybutylene oxide, styrene or its derivatives such as α-methylstyrene, indene, dicyclopentadiene, monomers which carry amino or imino groups, such as dimethylaminoethyl methacrylate, diethylaminoethyl acrylate, diethylaminopropyl methacrylamide or allylamine, monomers which carry quaternary ammonium groups, for example present as salts, as obtained by reacting basic amino functions with acids, such as hydrochloric acid, sulfuric acid, nitric acid, formic acid or acetic acid, or in quaternized form, e.g., dimethylaminoethyl acrylate hydrochloride, diallyldimethylammonium chloride, dimethylaminoethyl acrylate methylchloride, dimethylaminoethylaminopropylmethacrylamide methosulfate, vinylpyridinium salts or 1-vinylimidazolium salts; monomers in which the amino groups and/or ammonium groups are liberated only after the polymerization and subsequent hydrolysis, for example N-vinylformamide or N-vinylacetamide, and mixtures of two or more of the abovementioned monomers.

The monomers of the present invention may also include monomers having the general structure:

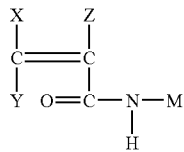

where X, Y, Z, and M may independently be a hydrogen, methyl, amine or group selected from an unsubstituted alkyl of two or more carbon atoms, substituted alkyl of two or more carbon atoms, linear alkyl of two or more carbon atoms, branched alkyl of two or more carbon atoms, cycloalkyl, alcohol, ether, polyether, amine, aralkyl radical, a substituted or unsubstituted aromatic, a substituted or unsubstituted heterocyclic, a substituted or unsubstituted olefinic hydrocarbon, a halogen atom, a substituted alkenyl group, unsubstituted alkenyl group, linear alkenyl group, branched alkenyl group, a substituted alkynyl group, unsubstituted alkynyl group, linear alkynyl group, branched alkynyl group, —CN, —CN, —S—CN, O—C=$NR_1$, —S—C=$NR_1$, —N=C=O, —C=$NR_1$, —$CR_1R_2$-Hal, —$CR_1R_2(OR_3)$ ($NR_4$), —$CR_1R_2(NR_3)(NR_4)$, an anhydride, acetal group, ketal group, an amidine group, —C=N—OH, —$N(R_1)$=$NR_2$, where $R_1$ to $R_4$, independently of one another in each case, are defined in the same way as X, Y, Z, and M above. The skilled artisan will recognize that the $R_1$ to $R_4$ may be substituted with, modified by the addition of or independently be an alkyl group, an alkylene group, an alkenyl group, an alkynyl group, an aryl group, an alkoxy group, an alkylcarbonyl group, an alkylcarboxyl group, an amido group, a carboxyl group or a halogen. Further more the R group may be substituted with one or more alkyl groups, alkylene groups, alkenyl groups, alkynyl groups, aryl groups, alkoxy groups, alkylcarbonyl groups, alkylcarboxyl groups, amido groups, carboxyl groups or halogens.

The amides of the present invention may be substituted, unsubstituted or modified N-alkyl or N-alkylamino-monosubstituted, or N,N-dialkyl-substituted or N,N-dialkylamino-disubstituted, in which the alkyl or alkylamino groups are derived from $C_1$-$C_{100}$ linear, $C_3$-$C_{100}$ branched-chain or $C_3$-$C_{100}$ carbocyclic units. Additionally, the alkylamino groups may be quaternized. Some examples include N,N-dimethylaminomethyl (meth)acrylate, N,N-diethylaminomethyl(meth)acrylate, N,N-dimethylaminoethyl (meth)acrylate, N,N-diethylaminoethyl(meth)acrylate.

Examples of suitable modified and unmodified monomers also include acrylic acid, methacrylic acid, ethylacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate isobutyl methacrylate, t-butyl methacrylate, 2-ethylhexyl methacrylate, decyl methacrylate, methyl ethacrylate, ethyl ethacrylate, n-butyl ethacrylat, isobutyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacryiate, glyceryl monomethacrylate, polyalkylene glycol(meth)acrylates, unsaturated sulfonic acids, such as, for example, acrylamidopropane sulfonic acid and combination there of.

Examples of the monomers for use in the present invention also include acrylamide, methacrylamide, ethacrylamide, N-methylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)propyl]methacrylamide, N-[3-(diethylamino)propyl]acrylamide; and combinations thereof.

The present invention reduces the growth of undesirable organisms, such as the bacteria genera *Staphylococcus, Pseudomonas, Salmonella, Shigella, Legionella, Methylobacterium, Klebsiella*, and *Bacillus*; the fungi genera *Candida, Rhodoturula*, and molds such as mildew; the protozoa genera *Giardia, Entamoeba*, and *Cryptosporidium*; the viruses poliovirus, rotavirus, HIV, and herpesvirus; and the algae genera *Anabaena, Oscillatoria*, and *Chlorella*; and other sources of biofouling on surfaces.

The present invention includes a method of forming rechargeable acyclic or aliphatic N-halamine polymers and fibers or synthesizing the acyclic or aliphatic N-halamine materials and adding them to a target material by solution blending, mechanical mixing, and/or thermal mixing. The materials processed into desired articles. The present invention also includes forming acyclic or aliphatic N-halamine containing polymers which includes adding precursors of the acyclic or aliphatic N-halamine polymer to a target material by solution mixing, mechanical blending, and/or thermal mixing. The mixtures are processed into desired articles, and then treated with halogen sources (e.g., chlorine bleach) to transform the precursors into active N-halamine materials.

The methods of the present invention can be readily used to incorporate acyclic or aliphatic N-halamine polymers or monomers into other materials to transform them into biocidal and biofilm-controlling materials. The resultant materials demonstrate potent antimicrobial activities against both gram-negative and gram-positive bacteria, yeast, fungus, virus, and spores and can reduce the attachment of bacteria, thus controlling biofilm formation on material surfaces. By selecting suitable acyclic or aliphatic N-halamine monomers for different materials, the acyclic or aliphatic N-halamine polymers can have a variety of characteristics known to the skilled artisan and/or polymer chemist.

In addition the type of polymer allows the control of distribution of the acyclic or aliphatic N-halamine monomers, e.g., segmented polymers, block polymers, multiblock polymers, gradient polymers, graft polymers, star polymers, branched polymers, multi-branched polymers and combinations thereof. The biocidal activity can be lost caused by extensive uses and/or prolonged storage, in which the N-halamine structures change back to the acyclic or aliphatic N-halamine precursors; however, because the compounds are not lost, the functions can be easily recharged by exposure to halogen sources (e.g., bleach solutions).

The present invention provides a practical, flexible and cost-effective application to transform a wide range of materials into durable and rechargeable biocidal and biofilm-controlling materials, which will find wide applications in medical devices, hospital equipment, water purification/delivery systems, food storage and food packaging, hygienic products, bio-protective applications, and other related challenging environment where self-decontamination of the material is needed.

The acyclic or aliphatic N-halamine materials of the present invention may be made and mixed with other materials prior, during or after material or article formation. The material of the present invention can be subjected to extrusion, injection molding, hot pressing, coating, painting, laminating, and solvent casting, mixtures and combinations thereof and formed into a bead, a film, a tube, a sheet, a thread, a suture, a gauze, a bandage, an adhesive bandage, a vessel, a container, a cistern, a filter, a membrane, a coating, a paint and combinations thereof.

In this invention, acyclic or aliphatic N-halamine may also be physically mixed with conventional and commercially important polymeric materials as antimicrobial additives. As long as the target polymeric materials can be dissolved in solvent(s), or can be melted, they can be manufactured into acyclic or aliphatic N-halamine containing polymeric materials, providing durable and rechargeable antimicrobial activities. Because dissolving and melting are conventional processing steps in the manufacturing of most polymeric materials, the present invention provides a universal technology to produce antimicrobial polymers. For polymeric materials that are not soluble and/or meltable, acyclic or aliphatic N-halamine materials can be painted or coated onto the polymeric materials.

The simple, practical, flexible and cost-effective acyclic or aliphatic N-halamines disclosed herein may be used as polymer additives in the range of about 0.01 to about 30.0 weight percent (wt. %), the typical range is about 0.1 to about 10.0 weight percent. Both solution and thermal blending can be used in the treatment. The acyclic or aliphatic N-halamines can be formed before or after mixing. The present invention will find wide applicability because it requires no new treatment steps, training and/or new equipment used in the transformation of conventional and commercially important polymers into durable and rechargeable antimicrobial materials.

The applications for use of the present invention include, e.g. antimicrobial treatment of plastics, rubbers, paints, coatings and fibers. The resulting materials may find applications in medical devices, hospital equipment, water purification/delivery systems, food storage and food packaging, hygienic products, consumer products, household items, bio-protective applications, and other related challenging environments where self-decontamination of the polymeric material is needed.

Microorganisms such as pathogenic bacteria, fungi, viruses, and spores have strong abilities to survive on fibrous materials.[1-10] Neely and Maley studied the survival of twenty-two multi-drug resistant gram-positive bacteria on hospital textiles. All the bacteria survived for at least one day, and some species survived for more than ninety days.[1] A continuous study found that gram-negative bacteria including *P. aeruginosa, E. coli, S. marcescens, P. mirabilis, K. pneumoniae, Acinetobacter* species and *Enterobacter* species survived on hospital/medical textiles from less than one hour to more than sixty days.[2] Medically important fungi, such as *Candida* spp., *Aspergillus* spp., *Fusarium* sp., *Mucor* sp., and *Paecilomyces* sp. survived on hospital fabrics from one day to several weeks.[3] In their serial studies, Sidwell et al reported that vaccinia virus, poliomyelitis virus and poliovirus could stay alive on cotton and wool fabrics for long periods of time, and the contaminated cloth transferred the viruses to other clean textiles through dry contact or laundering.[4-8] Barker and coworkers found that Norovirus survived on cleaning cloths; wiping hard surfaces with a contaminated cloth could spread the virus to hands, equipment and other surfaces.[9] Recently, the retention of *Aspergillus niger* spores on textile materials has also been reported.[10]

Contaminated textiles are often associated with increased risk of infections. The clear link between contaminated fibrous materials and diseases was first reported by Lister in 1867,[11] and this first report has been repeatedly confirmed in subsequent studies. For instances, Oliphant and colleagues reported a case that Q fever in hospital laundry workers was transmitted from contaminated clothing.[12] An outbreak of infection with *Salmonella typhimurium* in a large general hospital was traced to contaminated hospital fabrics,[13] and an outbreak of *Salmonella* gastroenteritis in a nursing home was attributed to soiled linens.[14] Orr and coworkers studied an outbreak of vancomycin-resistant *E. faecium* infection in a British hospital. They found that the bacteria were introduced into the hospital and acquired by the patients through rental therapeutic beds.[15]

In response to these challenges, much effort has been devoted to the development of infection-resistant textile materials for hospital, medical, bio-protective and related hygienic applications.[16-26] One of the most widely used approaches is to incorporate biocidal functional groups into fibrous materials. With this approach, antibiotics,[16,17] quaternary ammonium salts,[18] silver,[19] N-halamines,[20-26] etc., have been used to provide biocidal functions. The biocidal activities of these materials vary considerably. However, to the best of our knowledge, biocidal textiles that are capable of inactivating most medically relevant microorganisms including bacteria, fungi, viruses and spores have never been reported. Such textiles are needed in many hospital, medical, and bio-protective applications in which fast and broad-spectrum biocidal actions are required.

The present invention provides preparations and characterizations of antibacterial, antifungal, antiviral and anti-spore cellulosic fibrous materials. In our approach, methacrylamide (MAA) was grafted onto cotton cellulose, one of the most widely used hospital/medical textiles. After hypochlorite bleach treatment, part of the grafted MAA moieties was transformed into acyclic N-halamines, which demonstrated potent, durable and rechargeable biocidal effects against gram-negative bacteria, gram-positive bacteria, fungi, viruses, and spores.

In one example bleached cotton knit fabrics (e.g., Testfabrics Inc., West Pittston, Pa., No. 459) were used. Cerium (IV) ammonium nitrate ("CAN") and MAA were provided by VWR International, Inc. (e.g., West chester, Pa.). MAA was recrystallized from distilled water. Other chemicals were analytical grade and used as received.

Instrumentation. Fourier transform infrared (FT-IR) spectra were recorded on a Thermo Nicolet Avatar 370 FT-IR spectrometer (Woburn, Mass.). Thermal properties of the samples were examined on a Shimadzu DSC-60 instrument at a heating rate of about 10° C./minute under $N_2$ atmosphere.

Grafting MAA onto cotton cellulose. Before grafting, the cotton fabrics were washed in acetone at room temperature for one hour to remove impurities. About 1 gram of the fabric was immersed in about 40 mL of diluted nitric acid (about 0.004 mol/L) containing a known amount of CAN under $N_2$ atomophere.[27] The initiator was allowed to interact with cotton for thirty minutes. A pre-determined amount of MAA was then added into the solution. The solution was stirred for a certain period of time at a known temperature. At the end of the reaction, the grafted fabrics were removed and washed copiously with distilled water, dried at about 60° C. for twenty-four hours, and stored in a desiccator for seventy-two hours to reach constant weights.

Percentage graft yield was calculated according to the following equation:

$$\text{Graft \%} = \left(\frac{W_2 - W_1}{W_1}\right) \times 100 \qquad (1)$$

where W1 and W2 were the weights of the original and the grafted fabrics, respectively.

Chlorination. To transform part of the grafted MAA moieties in the fabrics into acyclic N-halamines, the grafted fabrics were immersed in about 0.6% NaOCl solutions in the presence of about 0.05% of a nonionic wetting agent (Triton X-100) at room temperature for a certain period of time under constant shaking. The bath ratio was kept at about 30:1, and the pH values of the solutions were adjusted with pH buffers. After chlorination, the samples were washed thoroughly with distilled water, air dried and stored in a desiccator for seventy-two hours to reach constant weights.

The active chlorine contents of the chlorinated MAA-grafted fabrics were determined by iodometric titration using a method reported previously.[20] Briefly, about 0.05 grams of the treated fabric was cut into fine powders, which were then treated with about one gram KI in about 40 millimeters distilled water (e.g., pH=about 4) at room temperature under constant stirring for sixty minutes. The formed $I_2$ was titrated with about 0.01 mol/L of standardized sodium thiosulfate aqueous solution. The same amount of un-chlorinated sample was also titrated using the same method as the control. Available active chlorine content of the chlorinated MAA-grafted sample was calculated according to equation 2:

$$Cl\% = \frac{35.5}{2} \times \frac{(V_{Cl} - V_0) \times 10^{-3} \times 0.01}{W_{Cl}} \times 100 \qquad (2)$$

where $V_{Cl}$ and $V_0$ were the volumes (mL) of sodium thiosulfate solutions consumed in the titration of the chlorinated and un-chlorinated samples, respectively; $W_{Cl}$ was the weight of the chlorinated sample (g).

Antibacterial functions. To ensure lab safety, the guidelines provided by the U.S. Department of Health and Human Services[28] were followed in all the microbial studies. *Escherichia coli* (*E. coli*, ATCC 15597, gram-negative bacteria) and *Staphylococcus aureus* (*S. aureus*, ATCC 6538, gram-positive bacteria) were used to challenge the antibacterial functions of the chlorinated MAA-grafted fabrics. Both species were purchased from American Type Culture Collection (e.g., ATCC, Manassas, Va.). The antibacterial tests were conducted following a modified AATCC (e.g., American Association of Textile Chemists and Colorists) Test Method 100-1999.

Briefly, *E. coli* and *S. aureus* were grown in broth solutions (e.g., LB broth for *E. coli*, tryptic soy broth for *S. aureus*) for about twenty-four hours at about 37° C. The bacteria were harvested by centrifuge, washed with phosphate buffered saline (PBS), and then resuspended in PBS to densities of $10^8$-$10^9$ colony forming units per milliliter (CFU/mL). 100 µL of the freshly prepared bacterial suspensions were placed onto the surfaces of four circular swatches of the chlorinated MAA-grafted cotton cellulose (e.g., about 2.0±0.1 cm² per swatch). After a certain period of contact time, the swatches were transferred into about 10 mL of sterilized sodium thiosulfate solution (e.g., about 0.03%), sonicated for about five minutes, and vortexed for about sixty seconds. Sodium thiosulfate solution at this concentration could quench the active chlorines in the fabrics without affecting the growth of the bacteria and the fungal, viral and spore species. The solution was serially diluted, and about 100 µl of each diluent were placed onto agar plates (e.g., LB agar for *E. coli*, tryptic soy agar for *S. aureus*). Colony forming units on the agar plates were counted after incubation at about 37° C. for about 24 hours. Pure cotton fabrics were tested under the same conditions as controls. Each test was repeated three times.

Antifungal functions. *Candida tropicalis* (*C. tropicalis*, ATCC 62690) provided by ATCC was selected as a representative example of fungi. In the antifungal tests, *C. tropicalis* was grown in YM broth at about 26° C. for about 48 hours, harvested, washed, and resuspended in PBS to densities of $10^8$-$10^9$ CFU/mL, as described above. About 100 µL of the freshly prepared fungal suspensions were placed onto the surfaces of four circular swatches of the chlorinated MAA-grafted cotton cellulose (e.g., about 2.0±0.1 cm² per swatch). After a certain period of contact time, the fabrics were transferred into 10 mL of sterilized sodium thiosulfate solution (e.g., 0.03%), sonicated for about 5 minutes and vortexed for about 60 seconds. The solution was serially diluted, and 100 µl of each diluent were placed onto YM agar plates. Colony forming units on the agar plates were counted after incubation at about 26° C. for about 48 hours. Pure cotton fabrics were tested under the same conditions as controls. Each antifungal test was repeated three times.

Antiviral functions. Stock solutions of MS2 virus (ATCC 15597-B1) were prepared using the agar overlay method suggested by ATCC. *E. coli* (ATCC 15597) was employed as the host for the MS2 virus. The stock solutions were diluted with PBS to $10^6$-$10^7$ plaque forming units per milliliter (PFU/mL) of the virus. About 100 µL of the freshly prepared viral suspensions were placed onto the surfaces of four circular swatches of the chlorinated MAA-grafted cotton cellulose (e.g., about 2.0±0.1 cm² per swatch). After a certain period of contact time, the fabrics were transferred into 10 mL of sterilized sodium thiosulfate solution (e.g., about 0.03%), sonicated for about 5 minutes, and vortexed for about 60 seconds. The solution was serially diluted, and about 100 µl of each diluent were placed onto LB agar plates containing a "lawn" of about 24 hour-old *E. coli* 15597 as the host. Plaque forming units on the agar plates were counted after incubation at about 37° C. for about 24 hours. Pure cotton fabrics were tested under the same conditions as controls. Each test was repeated three times.

Anti-spore functions. *Bacillus subtilis* spores obtained from North American Science Associates (e.g., Northwood, Ohio, lot no. N24609) were used to challenge the anti-spore functions of the treated fabrics. 100 µL of the spore stock solutions ($10^6$-$10^7$ spores/mL) were placed onto the surfaces of four circular swatches of the chlorinated MAA-grafted cotton cellulose (about 2.0±0.1 cm² per swatch). After a certain period of contact time, the fabrics were transferred into about 10 mL of sterilized sodium thiosulfate solution (e.g., about 0.03%), sonicated for about 5 minutes, and vortexed for about 60 seconds. The solution was serially diluted, and about 100 µl of each diluent were placed onto tryptic soy agar plates. Colony forming units on the agar plates were counted after incubation at about 37° C. for about 24 hours. Pure cotton fabrics were tested under the same conditions as controls. Each anti-spore test was repeated three times.

Scanning electron microscopy (SEM) observation. About 1 mL of each microbial suspension (e.g., $10^8$-$10^9$ CFU/mL of *E. coli* in PBS, $10^8$-$10^9$ CFU/mL of *S. aureus* in PBS, $10^8$-$10^9$ CFU/mL of *C. tropicalis* in PBS, or $10^6$-$10^7$ spores/mL of *Bacillus subtilis* in distilled water) was placed onto a chlorinated MAA-grafted cotton swatch (e.g., about 2.0±0.1 cm$^2$), respectively. After a certain period of contact time (e.g., about 5 minutes for *E. coli, S. aureus* and *C. tropicalis*, and 6 hours for *Bacillus subtilis* spores), the swatches were immersed into different broth solutions (e.g., LB broth for the swatches containing *E. coli*, tryptic soy broth for the swathes containing *S. aureus* or *Bacillus subtilis*, and YM both for the swatches containing *C. tropicalis*) and incubated at about 37° C. for about 24 hours (e.g., in the cases of *E. coli, S. aureus*, and *Bacillus subtilis*) or at about 26° C. for about 48 hours (e.g., in the case of *C. tropicalis*). The swatches were rinsed with about 0.1 M sodium cacodylate buffer (SCB) at pH about 7.4 (e.g., 3×30 mL) to remove loosely-attached cells, and then fixed with 3% glutaraldehyde in SCB at about 4° C. for about 24 hours. After being gently washed with SCB, the samples were dehydrated through an alcohol gradient,[18] dried in a critical point drier, mounted onto sample holders, sputter coated with gold-palladium, and observed under a LEO 1530 scanning electron microscope. The same procedure was also applied to pure cellulose fabrics as controls.

Durability and rechargeability of the biocidal functions. The treated cotton celluloses were tested for retention of biocidal functions under storage. Chlorinated MAA-grafted fabrics with known chlorine contents were stored in a conditioning room (e.g., about 25° C., about 65% relative humidity). The chlorine contents and the antibacterial, antifungal, antiviral and anti-spore functions were tested periodically over about 90-day storage time.

The durability was also tested after simulated usage/recharge cycles. In this experiment the chlorinated MAA-grafted fabrics were first treated with about 0.3% sodium thiosulfate solution at room temperature for about 60 minutes to quench the active chlorine, and then re-chlorinated using the same chlorination conditions of the original samples. After different cycles of this treatment, the chlorine contents and biocidal functions of the resultant fabrics were re-evaluated.

FIG. 1 is a schematic that illustrates the preparation of biocidal cotton cellulose. The preparation of the biocidal cotton cellulose comprises two basic steps, grafting and chlorination, as shown in FIG. 1. In grafting, MAA is grafted onto cotton fabrics using a well-established ceric ion technique.[27] After chlorination, part of the MAA moieties are transformed into acyclic N-halamines, providing potent, durable, and rechargeable biocidal functions against gram-negative bacteria, gram-positive bacteria, fungi, viruses, and spores.

Figure 2:
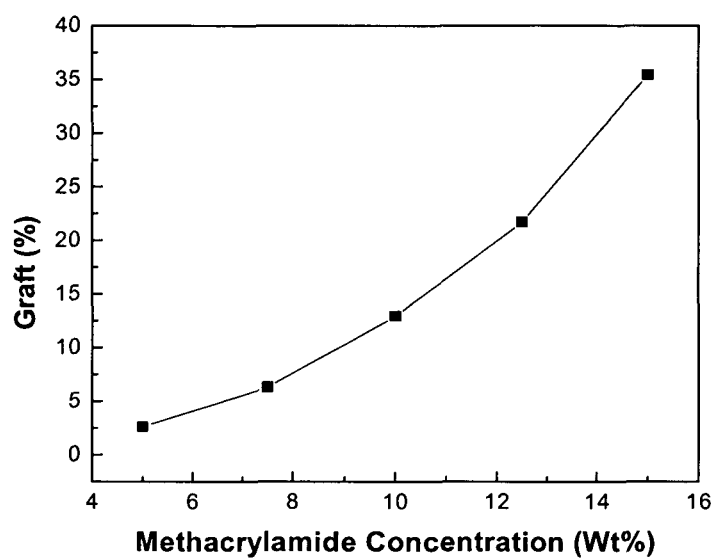
FIG. 2 is a graph of the effects of methacrylamide monomer concentration on percentage graft yield.

FIG. 2 is a graph of the effects of methacrylamide monomer concentration on percentage graft yield. Grafting MAA onto cotton cellulose. The influences of reaction conditions on grafting were investigated. FIG. 2 presents the effects of MAA concentration on percentage graft yield and a CAN concentration: $4 \times 10^{-3}$ mol/L; T=50° C.; t=3 hours. Keeping other conditions constant, increasing MAA concentration significantly increases graft yield. In this heterogeneous reaction system, the graft polymerization largely depends on the diffusion of the monomers into the inner parts of the cotton cellulose. As monomer concentrations go up, more monomers can reach the reactive sites on cotton molecules. Furthermore, increasing monomer concentration may increase the amount of MAA homopolymers, which will increase the viscosity of the solutions. This effect hinders terminations (particularly those through the coupling of growing polymer chains) and thus increases percentage graft yield.

Figure 3:
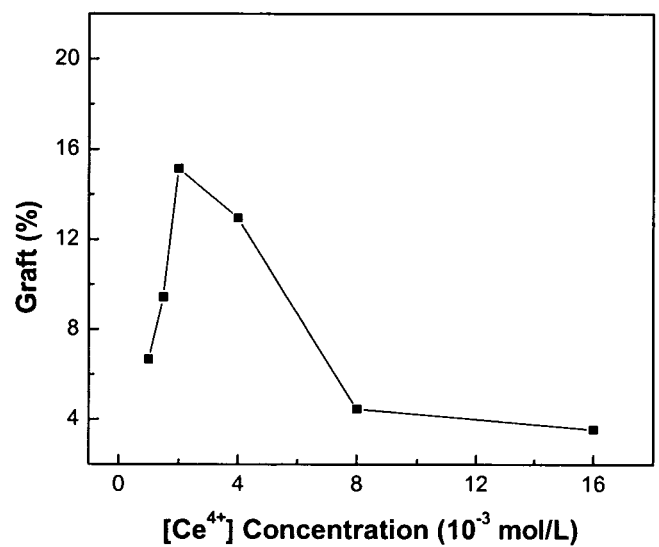
FIG. 3 is a graph of the effects of initiator concentration on percentage graft yield.

FIG. 3 is a graph of the effects of initiator concentration on percentage graft yield with the MAA concentration: 7 wt %; T=50° C.; t=3 hours. The effects of varying CAN concentration on the grafting reactions. Percentage graft yield increases and then decreases after an optimum value of $2.0 \times 10^{-3}$ mol/L. As the concentration of CAN increases, more cotton macro-radicals are formed, thereby increasing the graft yield. However, when the concentration of CAN is higher than the optimum value, further increase in initiator concentration may generate too much free radical, which will terminate the growing MAA side chains. Besides, high free radical concentration can promote chain transfer reactions to the monomers, which will result in the homopolymerization of MAA in the solutions and thereby decrease the concentrations of available MAA for the grafting reactions.[21]

Figure 4:
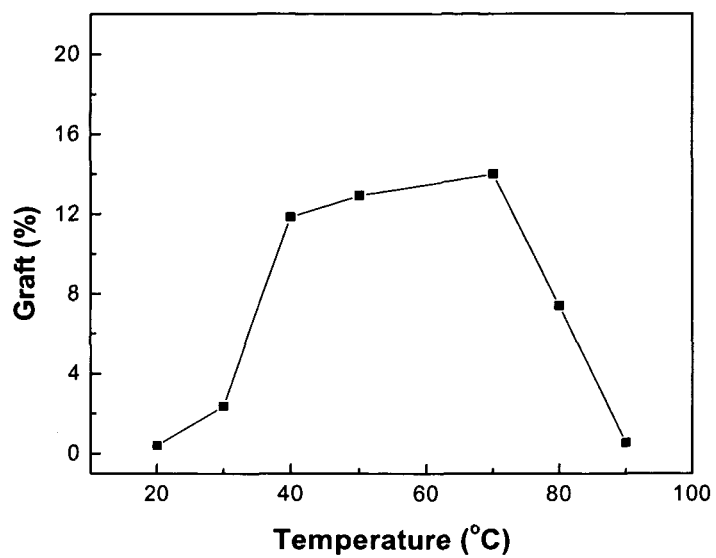
FIG. 4 is a graph of the effects of reaction temperature on percentage graft yield.

FIG. 4 is a graph of the effects of reaction temperature on percentage graft yield with a MAA concentration of 7 wt % and a CAN concentration of $4 \times 10^{-3}$ mol/L; t=3 hours. At lower than about 20° C., the graft yield is rather low. Thereafter, graft yield gradually increases with the increase of temperature up to about 70° C. Increasing temperature will significantly increase the swellability of cellulose, the diffusion rate of MAA, the decomposition rate of CAN, as well as the initiation rate and propagation rate of the grafting polymerization, and all these effects favor the grafting reactions. However, at even higher temperatures, termination rate of the graft polymerization may become too high, which can lead to lower percentage graft yield.

Figure 5:
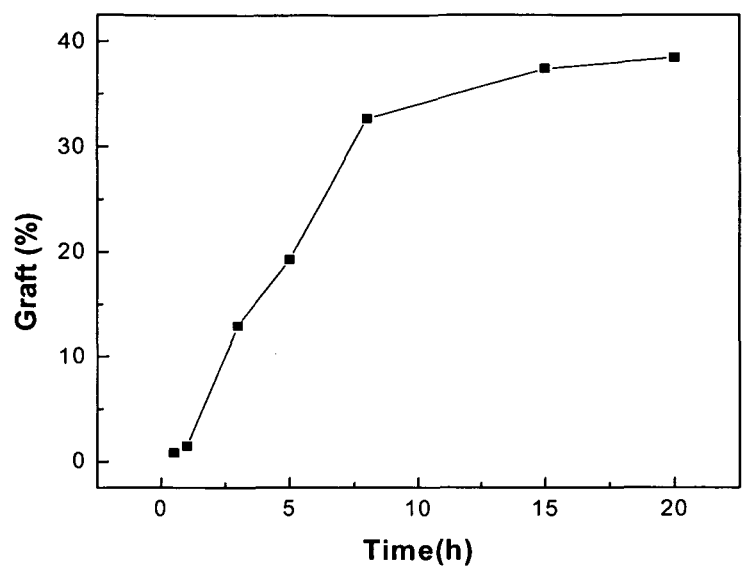
FIG. 5 is a graph of the effects of reaction time on percentage graft yield.

FIG. 5 is a graph of the effects of reaction time on percentage graft yield with a MAA concentration of about 7 wt % and a CAN concentration of $4 \times 10^{-3}$ mol/L; T=50° C. To provide further information on the grafting reactions, FIG. 5 shows the effects of reaction time on percentage graft yield. Increasing time up to about 8 hours considerably increases graft yield. After that, this effect becomes less obvious: after 8 h of grafting, the graft yield reaches about 32.7%; when the time is further extended to about 20 hours, the graft yield slightly increases to about 38.4%.

Figure 6:
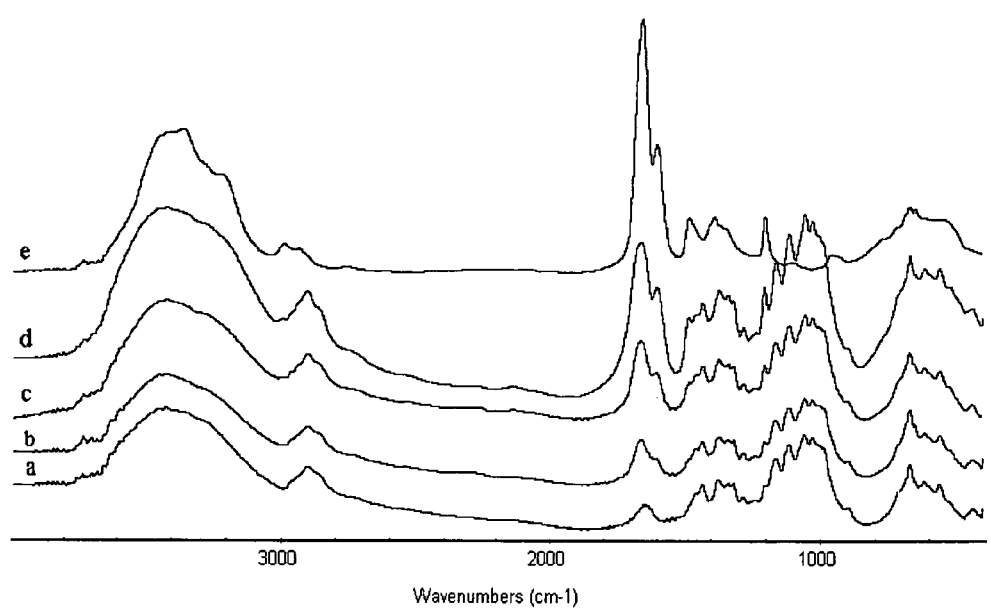
FIG. 6 is a FT-IR spectrum of the grafting reactions.

FIG. 6 is a FT-IR spectrum of the grafting reactions. Spectrum "a" is a FT-IR spectra of pure cotton; spectrum "b" is a FT-IR spectrum of MAA-grafted cotton with a graft yield of 12.9%. spectrum "c" is a FT-IR spectrum of MAA-grafted cotton with a graft yield of 21.7%. spectrum "d" is a FT-IR spectrum of MAA-grafted cotton with a graft yield of 32.7%. spectrum "e" is a FT-IR spectrum of pure PMAA.

In the spectrum of pure cotton cellulose (FIG. 6 spectrum a), the broad peak centered at about 3450 cm$^{-1}$ is attributable to the stretching vibration of the hydroxyl groups, and the weak band at about 1635 cm$^{-1}$ is caused by water of hydration.[20] In the spectrum of polymethacrylamide (PMAA, FIG. 6 spectrum e), the N—H stretching vibration band is at about 3357 cm$^{-1}$, and the amide I and amide II bands are presented at about 1650 and about 1600 cm$^{-1}$, respectively, which are in good agreement with the literature data.[29] In the spectra of the grafted samples (e.g., FIG. 6 spectrum b to spectrum d), the amide I and amide II bands can be clearly observed, whose intensities increase with the increase of percentage graft yield. These findings further suggest that MAA has been successfully grafted onto cotton cellulose.

Figure 7:
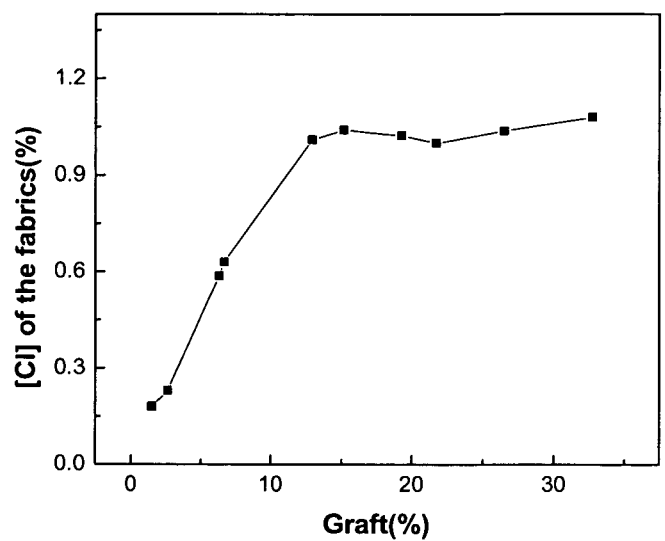
FIG. 7 is a graph of the effects of percentage graft yield on the active chlorine content of the chlorinated MAA-grafted fabrics.

Chlorination of the MAA-grafted cotton cellulose. FIG. 7 is a graph of the effects of percentage graft yield on the active chlorine content of the chlorinated MAA-grafted fabrics treated in about 0.6% NaOCl solution containing about 0.05% Triton X-100 at room temperature for 1 hour at pH=4; bath ratio: 30:1. Upon hypochlorite bleach treatment, acyclic N-halamines are formed in the grafted MAA side chains, as illustrated in FIG. 1. The effects of percentage graft yield on the active chlorine contents of the fabrics are shown in FIG. 7. With the increase of graft yield up to about 12.9%, chlorine content rapidly increases to around 1.0%; thereafter, a relatively constant value is obtained. A comparison of percentage graft yield and chlorine content of the resultant fabrics indicate that upon hypochlorite treatment, only part of the amide groups in the grafted MAA side chains are transformed into N-halamines (—$NH_2$→—NHCl). For instance, at a percentage graft yield of about 1.45%, if all the —$NH_2$ are transformed, a chlorine content of about 0.61% would be obtained. However, iodometric titration shows that the resultant fabric contains about 0.18% active chlorine, suggesting a chlorination rate of about 29.5% (i.e., only about 29.5% of the amide groups are chlorinated). With the increase of percentage graft yield, the chlorine content increases, but the chlorination rate gradually decreases: at a graft yield of about 6.3%, the chlorination rate is about 22.3% (e.g., about 2.82% of the "theoretical" chlorine content vs. about 0.63% of the observed chorine content); when the graft yield increases to about 12.9%, the chlorination rate decreases to about 18.5% (e.g., about 5.46% of the "theoretical" chlorine content vs. about 1.0% of the observed chlorine content). Increasing chlorination time form about 1 hour to about 4 hours has little effect on the chlorine content and chlorination rate. Similar trend has also been reported in the chlorination of other polymeric amides, which may be caused by the steric hindrance of the neighboring amide groups during chlorination reactions.[23]

Figure 8:
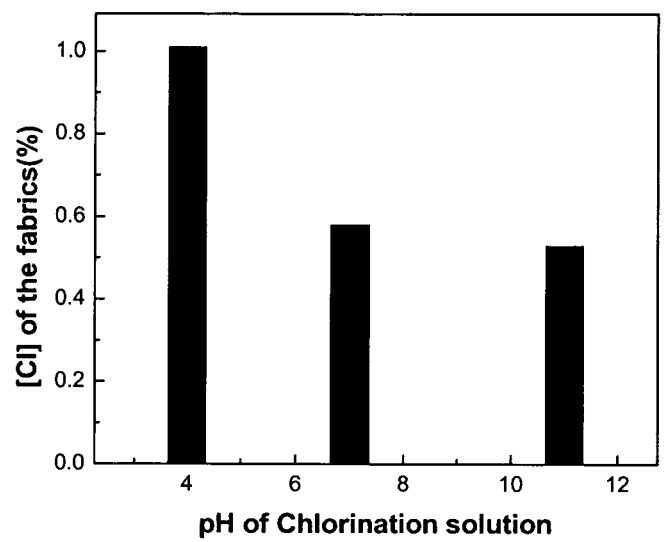
FIG. 8 is a graph illustrating the effect of pH on the chlorination reactions.

FIG. 8 is a graph illustrating the effect of pH on the chlorination reactions. It was found that the chlorination reactions were markedly enhanced under weak acidic conditions. In addition to percentage graft yield, chlorination conditions such as pH values also affect the active chlorine content of the fabrics. The effects of pH value on the active chlorine content of the chlorinated MAA-grafted fabrics (e.g., graft % of the fabrics: about 12.9%; chlorination condition: about 0.6% of NaOCl solutions; about 0.05% Triton X-100; bath ratio:about 30:1. The fabrics were chlorinated at room temperature for 1 hour.) As shown in FIG. 8, with a percentage graft yield of about 12.9%, keeping other conditions constant, at pH=about 11, the chorine content of the resultant fabric is about 0.53%; at pH=about 7, the chlorine content increases slightly to about 0.58%. However, when the pH value is dropped to about 4, the chlorine content of the treated fabric reaches as high as about 1.0%.

Similar result has been reported in the chlorination of other polyamides, which is believed to be attributed to the different chlorination mechanisms under basic and acidic conditions.[23] In basic conditions, the first step of the chlorination of amides is the formation of a six-member O-chlorinated intermediate, followed by subsequent rearrangements to the more stable N-chlorinated products.[30,31] In acidic conditions, however, the chlorinating reactions might proceed via direct substitutions of the hydrogen atoms by $Cl^+$ at the nitrogen atoms.[32] Apparently, this reaction is much easier than the "intermediate-rearrangement" pathway under basic conditions, and this leads to much higher active chlorine contents on the fabrics when acidic conditions are used.

A possible side reaction during chlorination is the Hoffmann-type degradation of the amide groups in the grafted MAA side chains, particularly under basic conditions.[32] To verify this effect, fabrics with different original percentage graft yields (e.g., about 1.45%, 6.3%, 12.9%, 21.7, and 32.7%) were chlorinated with about 0.6% NaOCl solution at pH about 4, 7, and 11, respectively, at room temperature for 1 hour. After chlorination, the fabrics were treated with about 0.3% sodium thiosulfate to quench the active chlorine, and washed and dried. The resultant fabrics were treated with about 1% ninhydrin aqueous solution at about 100° C. for about 30 minutes. No color change could be detected on any of the fabrics. The same fabrics were re-chlorinated and re-quenched, and after about 10 cycles of repeated bleaching and quenching, the ninhydrin tests were still negative. Because the ninhydrin test could detect the presence of amino groups to a level of about 0.1 μmol,[33] these findings suggest that in the current study, stable acyclic amide N-halamines were formed in the grafted MAA side chains. The Hoffmann-type degradation was not observed, which could be caused by the relatively mild chlorination conditions used. Similar results were also obtained in the bromination of polyacrylamide.[34]

Figure 9:
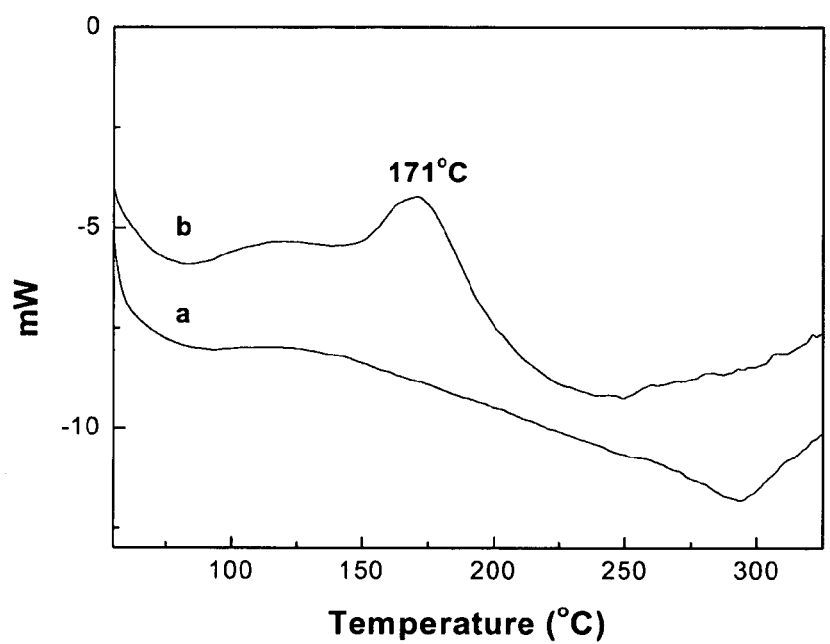
FIG. 9 illustrates DSC curves of (a) un-chlorinated MAA-grafted fabric and (b) chlorinated MAA-grafted fabric.

FIG. 9 illustrates DSC curves of (a) un-chlorinated MAA-grafted fabric and (b) chlorinated MAA-grafted fabric (e.g., active chorine content of about 1.0%). To provide further information on chlorination, FIG. 9 shows the DSC curves of the chlorinated and un-chlorinated MAA-grafted fabrics at a percentage graft yield of about 12.9%. The chlorinated sample shows an exothermic peak at about 171° C. (FIG. 8b); the same peak is not observed in the DSC curve of the un-chlorinated fabric. The 171° C. peak is most likely attributable to the decomposition of the N—Cl bond, which is in good agreement with our previous studies.[35] These findings further confirm the —NH2→—NHCl transformation upon hypochlorite bleach treatment, as shown in FIG. 1.

Biocidal functions of the chlorinated MAA-grafted fabrics. The chlorinated MAA-grafted fabrics demonstrate potent biocidal efficacy against a wide range of microorganisms. Shown in Table 1 are typical biocidal results against gram-negative bacteria, gram-positive bacteria, fungi, and viruses. At about 0.5% chlorine content, the fabrics provide a total kill of $10^8$-$10^9$ CFU/mL of *E. coli*, *S. aureus*, and *C. tropicalis* in only about 3 min. On the other hand, MS2 virus appears to be more resistant than the bacterial and fungal species tested: at the same chlorine content, it takes 30 minutes for the fabrics to offer a total kill of $10^6$-$10^7$ PFU/mL of the virus. When the chlorine content is increased to about 1.0%, however, the contact time for a total kill of the virus decreases to about 5 minutes. These exceptional biocidal activities point to great potentials of the new cotton cellulose for a wide range of infection-resistant applications, particularly for applications in which fast and broad-spectrum efficacies are required.

TABLE 1 illustrates the antibacterial, antifungal and antiviral efficacies of the chlorinate MAA-grafted fabrics.

| Microorganisms | Chlorine content | Minimum contact time for a total kill |
| --- | --- | --- |
| *E. coli*\* | 0.5% | 3 min |
| *S. aureus*\* | 0.5% | 3 min |
| *C. tropicalis*\* | 0.5% | 3 min |
| MS2 virus\*\* | 0.5% | 30 min |
| MS2 virus\*\* | 1.0% | 5 min |

\*Bacterial or fungi concentration: about 108-109 CFU/mL and
\*\*Viral concentration: about 106-107 PFU/mL.

Compared with bacteria, fungi and viruses, spores are much more difficult to kill. Spore coat, cortex and inner protoplast have been identified as possible barriers against the attack of biocidal agents.[36] Although the anti-spore effects of inorganic disinfects including free chlorine, iodine, ozone, and nitrous acid have been investigated,[36-39] polymeric materials that are capable of inactivating spores have never been reported. In this investigation we use *Bacillus subtilis* spore to challenge the biocidal functions of the chlorinated MAA-grafted fabrics. This a tough spore, which has been used as biological indicators in sterilizations as well as surrogates of anthrax spores.[36]

Figure 10:
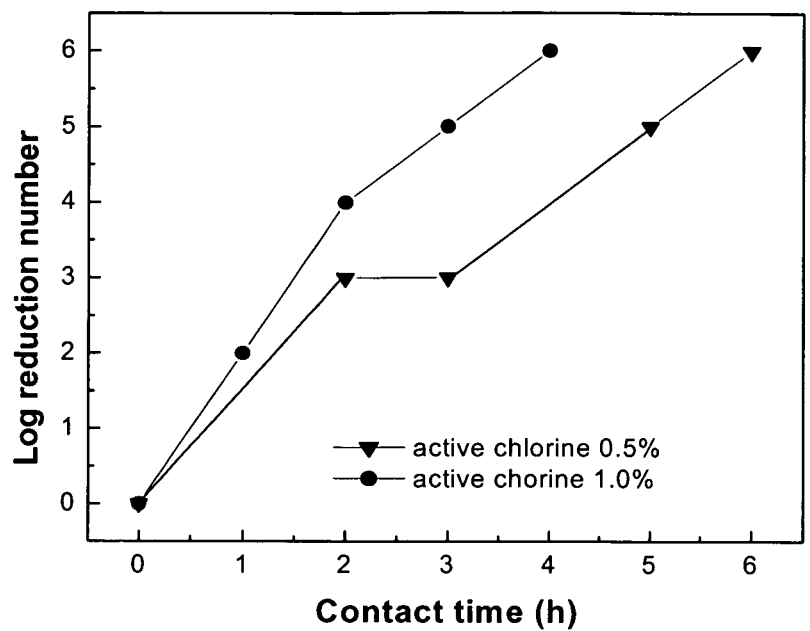
FIG. 10 illustrates typical anti-spore results of the chlorinated MAA-grafted cotton cellulose fabrics.
Figure 11A:
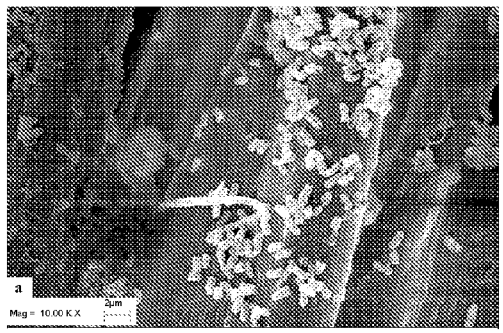
FIGS. 11A-11J are SEM images of SEM results of the biocidal effects of the samples.
Figure 11B:
Figure 11C:
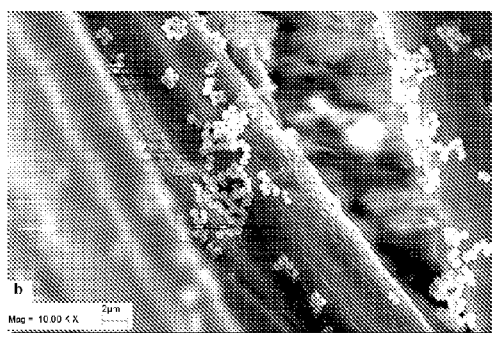
Figure 11D:
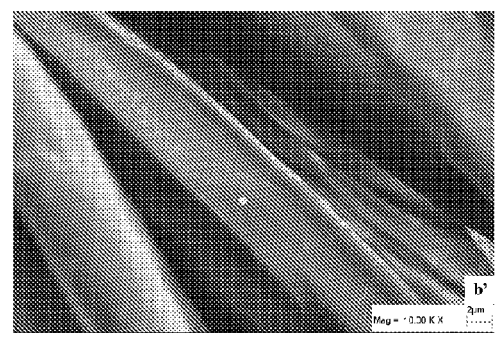
Figure 11E:
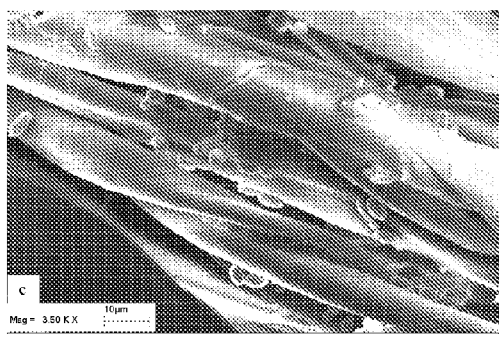
Figure 11F:
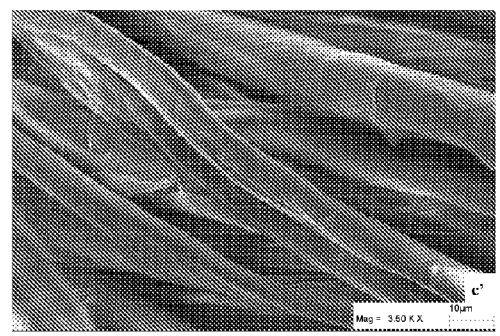
Figure 11G:
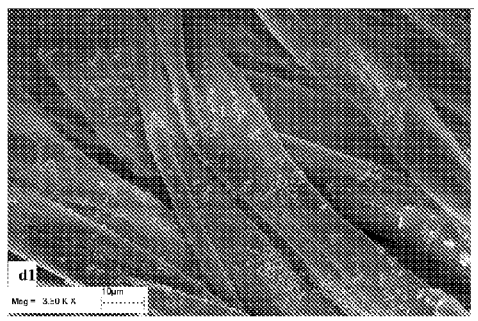
Figure 11H:
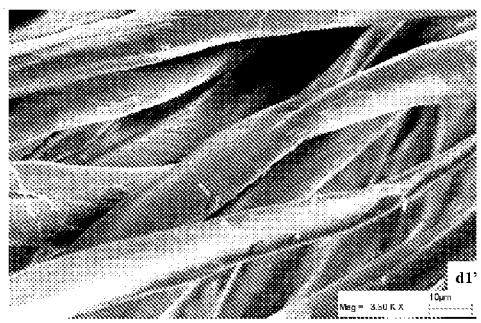
Figure 11I:
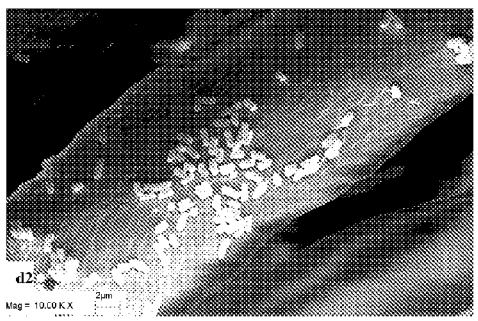
Figure 11J:
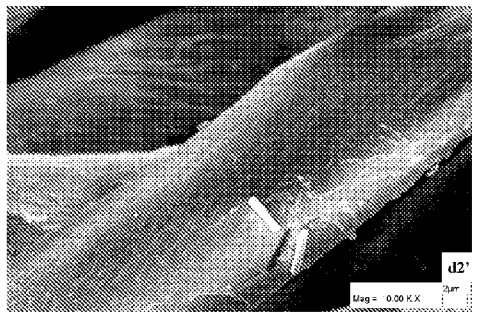

FIG. 10 illustrates typical anti-spore results of the chlorinated MAA-grafted cotton cellulose fabrics. The original spore concentration is in the range of about $10^6$-$10^7$ spores/mL. The most striking finding is that the new fabrics are able to provide a total kill of the spores, further suggesting the potentials of the new fabrics for infection-resistant applications. The anti-spore activities are affected by the chlorine contents of the samples: while fabrics with about 0.5% of active chlorine content kill all the spores tested in 6 hours, fabrics containing about 1.0% of active chlorine inactivate the same amount of Bacillus subtilis spores within about 4 hours. These findings are not surprising: the biocidal action of N-halamines has been reported to be a manifestation of a chemical reaction involving the direct transfer of positive halogens from the N-halamines to appropriate receptors in the microorganisms.[20-26] This reaction could effectively destroy or inhibit the enzymatic or metabolic process, leading to the expiration of the microorganisms. As a result, higher chlorine active contents lead to more potent biocidal efficacies. The present invention provides anti-spore functions in both the vegetative and non-vegetative states FIG. 11 is an SEM image of SEM results of the biocidal effects of the samples: (a) untreated fabric challenged with E. coli, (a') treated fabric challenged with E. coli; (b) untreated fabric challenged with S. aureus, (b'), treated fabric challenged with S. aureus, (c) untreated fabric challenged with C. tropicalis, (c') treated fabric challenged with C. tropicalis, (d1') untreated fabric challenged with Bacillus subtilis, low magnification, (d1') treated fabric challenged with Bacillus subtilis, low magnification, (d2) untreated fabric challenged with Bacillus subtilis, high magnification, (d2') treated fabric challenged with Bacillus subtilis, high magnification.

The antibacterial, antifungal and anti-spore functions of the chlorinated MAA-grafted fabrics were also characterized with SEM. As shown in FIG. 11, after about 1 day of incubation, a large amount E. coli, S. aureus, C. tropicalis or Bacillus subtilis adhere to the swath of pure cotton cellulose, e.g., see FIG. 11, a-d2. On the chlorinated MAA-grafted samples containing about 1.0% of active chlorine (e.g., see FIG. 11, a'-d2'); however, fewer adherent microorganisms could be observed, further suggesting the potent biocidal functions of the new cotton cellulose.

Durability and rechargeability are two other important features of the chlorinated MAA-grafted cotton cellulose. At about 21° C. and about 65% relative humidity, the samples have been stored for more than three months without any significant change in the active chlorine content on the fabrics as well as the biocidal efficacies against the bacterial, fungal, viral and spore species. Fabrics containing about 1.0% of chlorine (e.g., percentage graft: about 12.9%) have also been treated with about 0.3% sodium thiosulfate to quench the active chlorine and then re-bleached with about 0.6% of NaOCl at pH 4 at room temperature for about 1 hour. After about 10 cycles of the "quenching-bleaching" treatments, the chlorine contents and biocidal activities of the fabrics are essentially unchanged, indicating that the biocidal functions are fully rechargeable.

The present invention may include one or more of the following groups or modifications to the polymer, the fiber, the acyclic N-halamine, the halamine: "alkyl," "alkylene" "heteroalkylenes," "alkoxy," "alkylamino," "alkylthio" and "thioalkoxy," "heteroalkyl," "cycloalkyl," "heterocycloalkyl," "halo" or "halogen," "haloalkyl," "monohaloalkyl," "polyhaloalkyl," "aryl," "aryloxy," "arylthioxy," "arylalkyl," "arylalkyl," "acyl" or other modification known to the skilled artisan.

For example some compounds include (3E)-N-Butylpent-3-enamide, 2-(2-Methylcyclopropyl)acetamide, (3E)-N-Butylhex-3-enamide, (3E)-3-Methyldec-3-enamide 3-Isopropylbut-3-enamide, (3E)-Pent-3-enethioamide, (2R,3E)-N-Butyl-2-[(S)-Hydroxy(Phenyl)methyl]hex-3-enamide, 2-Cyclohex-1-en-1-yl-N-[(2S)-2-Formyl-1-Propylbutyl]Acetamide, N-[(2S)-2-Formyl-1-Propylbutyl]-3-Methylbut-3-enamide, (3E)-N-[(2S)-2-Formyl-1-Propylbutyl]pent-3-enamide, N-[(2S)-2-Formyl-1-Propylbutyl]Acetamide, 4,5-Dimethyl-3,6-Dihydro-2H-Pyran-3-Carboxamide, 2-(5-Methyl-3,6-Dihydro-2H-Pyran-4-yl)Acetamide, Methyl-5-Bromopentanoate, Diethyl Bromo(Methyl)malonate, Ethyl (Methylthio)Acetate, Ethyl 2-Phenoxypropanoate, Iso-Butyl Hexanoate, n-Propyl Hexanoate, Ethyl 2-Ethylacetoacetate, 5-Bromopentylacetate and derivatives thereof. In addition amines and amines containing a base-forming nitrogen atom as a substituent thereof, bifunctional amines, polyfunctional amines, and amino-group-containing polymers may also be used.

In addition, the polymer may be made include copolymer of natural product such as gelatin, a cellulose derivative, or casein. In addition, derivatives may be used to analogously alter or modify the cellulose or other substrate used in the present invention.

In addition, the present invention may be used with microbial cellulose. For example, microbial cellulose may be biosynthesized in the presence of a substance which acts to decrease the order of cellulose fibrillar structure, e.g., as taught in U.S. Pat. No. 4,942,128. In addition, the present invention may be used in conjunction with microbial cellulose that has properties depending upon the particular processing steps employed, e.g., optical clarity; increased absorptive capacity; improved ability to retain absorptive capacity through cycles of wetting and drying; tensile strength; resilience, and elasticity. Other cellulose derivatives may be used to analogously alter the cellulose produced by cellulose-producing microorganisms. For example, other polysaccharide derivatives may be substituted and compositions described herein. These polysaccharide derivative substitutes include polysaccharides such as cellulose, starch or dextran having substituents groups such as alkyl, alkylcarboxy, alkylhydroxy, sulfate, sulfonic acid, or alkylphosphate. These derivatives are most preferably hydrophilic although cellulose itself is so hydrophilic that minor amounts of hydrophobic substituents such as methyl may be used.

In addition, the acyclic N-halamine may be N-vinylformamide, N-vinylacetamide, vinylpyrrolidone, acrylamide, diacetoneacrylamide, N,N-dimethylacrylamide, vinylpyridine, methacrylamide, or allylthiourea may be used with the present invention.

Furthermore, the acyclic N-halamine may contain acrylic or methacrylic acid, an alkyl ester or alkylaminoalkylamide of acrylic or methacrylic acid, styrene, a N—$C_1$-$C_4$ dialkylamino-$C_1$-$C_4$ alkyl ester of acrylic or methacrylic acid, an acrylamide or a methacrylamide, a N-substituted acrylamide or methacrylamide, a N—$C_1$-$C_4$ dialkylamino-$C_1$-$C_4$ alkylacrylamide or -methacrylamide, acrylonitrile or methacrylonitrile, acrolein, a derivative of acrolein, vinyl acetate, 1-vinylpyrrolidone, 1-vinylimidazole and 2- or 4-vinylpyridine or precursors or derivatives thereof.

In addition the present invention may be made mixed with one or more material prior, during or after combining to materials for article formation and provide biocidal activity. The material or material precursor of the present invention can be subjected to extrusion, injection molding, hot pressing, coating, painting, laminating, and solvent casting, mixtures and combinations thereof and formed into a bead, a film, a tube, a sheet, a thread, a suture, a gauze, a bandage, an adhesive bandage, a vessel, a container, a cistern, a filter, a membrane, a coating, a paint and combinations thereof.

The present invention includes a method of forming acyclic N-halamine-containing materials, which includes synthesizing the acyclic N-halamines, acyclic N-halamines monomers or acyclic N-halamines precursors, and adding the acyclic N-halamines, acyclic N-halamines monomers or acyclic N-halamines precursors to the target materials by solution blending, mechanical mixing, coating, painting, laminating, and/or thermal mixing. The mixtures can be used directly or can be processed into desired articles.

The present invention also includes adding precursors of the N-halamines to the target materials by solution mixing, mechanical blending, coating, painting, laminating, and/or thermal mixing. The mixtures or the articles processed from the mixtures are then treated with halogen sources (e.g., chlorine bleach) to provide the antimicrobial, anti-biofilm, and/or photo and thermal stabilizing functions.

The desired functions can be lost caused by extensive uses and/or prolonged storage, in which the N-halamine structures change back to the precursors; however, because the compounds are not lost, the functions can be easily recharged by a simple exposure to halogen sources (e.g., bleach solutions).

The present invention provides a practical, flexible and cost-effective application to transform a wide range of materials into durable and rechargeable biocidal and biofilm-controlling materials, which will find wide applications in medical devices, hospital equipment, water purification/delivery systems, food storage and food packaging, hygienic products, bio-protective applications, and other related challenging environment where self-decontamination of the material is needed.

Various materials can be treated using the methods of the present invention. Polymers, monomers, fabrics, fibers materials and so forth suitable for use in the present invention include, but are not limited to, a plastic, a rubber, a textile material, a paint, a surface coating, an adhesives, cellulose, a polyester, wood pulp, paper, an absorbent, and a polyester/cellulose blend, inorganic substances such as glass, metallic and ceramic.

In addition the present invention may be made mixed with one or more material prior, during or after combining to materials for article formation and provide biocidal activity. The present invention may be an additive for polymers, coatings, stains, paints and so forth, or may itself be a coating, stain, paint and so forth. The material or material precursor of the present invention can be subjected to extrusion, injection molding, hot pressing, coating, painting, laminating, and solvent casting, mixtures and combinations thereof and formed into a bead, a film, a tube, a sheet, a thread, a suture, a gauze, a bandage, an adhesive bandage, a vessel, a container, a cistern, a filter, a membrane, a coating, a paint and combinations thereof.

The present invention includes a method of forming acyclic N-halamine-containing materials, which includes synthesizing the acyclic N-halamines, acyclic N-halamines monomers or acyclic N-halamines precursors, and adding the acyclic N-halamines, acyclic N-halamines monomers or acyclic N-halamines precursors to the target materials by solution blending, mechanical mixing, coating, painting, laminating, and/or thermal mixing. The mixtures can be used directly or can be processed into desired articles.

The present invention also includes adding precursors of the acyclic N-halamines to the target materials by solution mixing, mechanical blending, coating, painting, laminating, and/or thermal mixing. The mixtures or the articles processed from the mixtures are then treated with halogen sources (e.g., chlorine bleach) to provide the antimicrobial, anti-biofilm, antiodor and/or photo and thermal stabilizing functions.

The desired functions can be lost caused by extensive uses and/or prolonged storage, in which the acyclic N-halamine structures change back to the precursors; however, because the compounds are not lost, the functions can be easily recharged by a simple exposure to halogen sources (e.g., bleach solutions).

The present invention provides a practical, flexible and cost-effective application to transform a wide range of materials into durable and rechargeable biocidal and biofilm-controlling materials, which will find wide applications in medical devices, hospital equipment, water purification/delivery systems, food storage and food packaging, hygienic products, bio-protective applications, and other related challenging environment where self-decontamination of the material is needed.

Various materials can be treated using the methods of the present invention. Polymers, monomers, fabrics, fibers materials and so forth suitable for use in the present invention include, but are not limited to, a plastic, a rubber, a textile material, a paint, a surface coating, an adhesives, cellulose, a polyester, wood pulp, paper, an absorbent, and a polyester/cellulose blend, inorganic substances such as glass, metallic and ceramic.

Various materials can be treated using the methods and compositions of the present invention including polymers, monomers, fabrics, fibers materials and so forth. These materials can be used in consumer carpeting for pet owners, commercial carpeting, residential housing, anti-mold grout, anti-mold caulk, safe water storage, anti-slime filters, anti-mold filters, pools filters and spas filters, antiviral masks, Wound dressings, Floor sealing systems, and wall sealing systems, catheters (e.g., venous, urinary, tracheal, dialysis), Medical packaging, Food packaging, Fabric laminations (e.g., film, net and adhesive), Footwear (anti-odor and anti-fungal), Military coatings, Incontinence products (e.g., bed pads and patient wear) and combinations thereof.

The polymeric plastics suitable for the present invention also include thermoplastic or thermosetting resins. The thermoplastics include, but are not limited to, polyethylene, polypropylene, polystyrene, and polyvinylchloride. Thermoplastics also include but not limited to polyamideimide, polyethersulfone, polyarylsulfone, polyetherimide, polyarylate, polysulfone, polycarbonate and polystyrene. Additional thermoplastics include, but are not limited to, polyetherketone, polyetheretherketone, polytetrafluoroethylene, nylon-6,6, nylon-6,12, nylon-11, nylon-12, acetal resin, polypropylene, and high and low density polyethylene. The present invention is also suitable for the treatment of plastics, rubbers, paints, coatings, and fibers, including, but not limited to, polyolefins, polystyrene and its derivatives, ABS, EPDM, cellulose acetate, polyurethane, etc.

The plastics and fabrics made using the present invention are anti-bacterial, anti-viral, anti-fungal and anti-odor with activity greater than silver-impregnated plastics and fabrics, the next-best approach. The present invention includes plastic parts, films, tubing, cotton and synthetic fabrics and antimicrobial plastic additive that are antimicrobial in nature. The plastic additive is compatible with standard plastics including PET, polyethylene, PVC, polypropylene, and polystyrene. Fiber and fabric manufacturers can use the plastic additive without altering their normal fiber extrusion process. Polyester, nylon, and polypropylene fabrics can now be made permanently antimicrobial.

Additionally, low-melt-temperature plastics such as polystyrene, PVC and Polyethylene can be pre-chlorinated by adding the present invention to plastics to include non-woven fabrics, e.g., masks, wipes, shoe and head covers, diapers, wound care, and disposable healthcare fabrics, disposable medical plastics and packaging e.g., medical packaging to ensure sterility, food packaging to protect against bacteria, anti-mold packaging to extend shelf-life.

Additionally, low-melt-temperature plastics such as polystyrene, PVC and Polyethylene can be pre-chlorinated by adding the present invention to plastics to include non-woven fabrics, e.g., masks, wipes, shoe and head covers, diapers, wound care, and disposable healthcare fabrics, disposable medical plastics and packaging e.g., medical packaging to ensure sterility, food packaging to protect against bacteria, anti-mold packaging to extend shelf-life. Additional applications of the present invention are listed in Tables 2 and 3 below.

TABLE 2

| Antimicrobial Plastic Additive | Product Examples |
|---|---|
| Carpet and Upholstery | Healthcare carpeting. Anti-infection (e.g., bacteria, viruses, and funguses). Anti-odor. Consumer carpeting for pet owners. |
| Cleaning Tools | Consumer, healthcare, dental, food service, food factory. Rags. Mops. Sponges. Disposables, nonwoven wipes, etc. Toothbrushes. |
| Gloves | Anti-infection, anti-cross contamination gloves for healthcare, food factory, food service. Nitrile. Vinyl. Knit. |
| Medical Nonwovens (garments/masks) | Develop antibacterial, antiviral nonwoven products (e.g., disposable and reusable) for healthcare, food factory, food service, first responders (e.g., medics, fire-fighters) and military (e.g., anti-germ warfare). Antiviral masks. Wound dressings. Patient and staff apparel (e.g., scrub apparel and patient gowns). Tapes and electrodes. Filter media. Hot/cold therapy bags. Stretcher covers. Shoe & head covers. Isolation gowns. Fabrics for wound dressings, prep pads, finger bandages, operation swabs, medical tape base, medical wipes, hospital bed linens and ostomy bags. Disposable absorbent pads (e.g., medical underpads for nursing homes and operating rooms, ambulance floor pads, trauma pads for bodily contact, lab bench pads, transportation containment pouches, etc. |
| Water/Air Filtration | Anti-slime filters, e.g., pools and spas. Healthcare filtration, e.g., anti-slime filters in dialysis machines, endoscope cleaning machines, etc. Drinking water purification and storage. Industrial water treatment. Consumer, industrial and healthcare air filtration. |

TABLE 2-continued

| Antimicrobial Plastic Additive | Product Examples |
|---|---|
| Food Processing/manufacturing | Cross-contamination protection. Floor and wall sealing systems. Uniforms and gloves. Conveyor belts. Cutting boards. Food film covering. |
| Paints and Coatings | Paints. Film covering. Stains. |
| Medical Devices | Catheters (e.g., venous, urinary, tracheal, dialysis). Instruments (e.g., stethoscopes, blood pressure cuffs). Patient touch surfaces (e.g., mattresses, bed railings, slings, bathroom surfaces). |
| Wound Care and Chronic Skin Infections | Pads. Sponges. Bandages. Burns. Chronic Wound. Dermal Lesions. Diabetic Neuropathic Foot Ulcer. Edema. First and Second-Degree Burns. Infected Wound. Necrotic Wound. Neuropathic Ulcer. Skin at Risk from Radiation Complications, Excess Moisture, Skin Grafts, Stage I, II, III, IV Pressure Ulcers, Surgical Incisions. |
| Packaging | Medical packaging to ensure sterility. Food packaging to protect against bacteria. Anti-mold packaging to extend shelf-life. |

TABLE 3

| Antimicrobial Textiles | Product Examples |
|---|---|
| Medical Textiles | Reusable healthcare textiles for acute care, long-term care, dental industries to provide infection protection against microbes including bacteria, viruses, and funguses. Sheets and pillow cases. Patient wear. Uniforms for nurses, doctors, cleaning staff, dentists. Privacy curtains. Toweling. Fabric laminations (e.g., film, net and adhesive). Incontinence products (e.g., bed pads and patient wear). Antiviral woven reusable masks (e.g., Avian Influenza). Medical barriers. |
| Military Textiles | Underwear and socks. Battle dress uniforms. Anti-germ warfare uniforms. |
| Apparel and linen | Fitness club members, Sports Leagues, Hotels, Gaming Casinos, Linens and uniforms for food service operations, food factories, and prison inmates. Outer wear, socks, underwear. Outdoor and hunting apparel. Footwear (anti-odor and anti-fungal). |
| Medicated Products Consumer Disposable Nonwovens | Medicated socks and underwear. Wound care. Adult incontinence disposable diapers (e.g., anti-odor). Baby diapers (e.g., anti-diaper rash). Feminine hygiene products (e.g., tampons, pads). Home wipers for cleaning. |

| Antimicrobial Textiles | Product Examples |
|---|---|
| Building Products | Biofilm remediation for plastic tubing and pipe applications in these markets: potable water storage, PVC potable water plumbing and piping in chlorinated systems (e.g., municipal and construction), medical tubing, dental tubing, manufacturing process water. Anti-mold grout and caulk. Anti-mold wall board. Countertops and flooring. Anti-mold, antimicrobial paints and coatings. Low-cost water purification (low chlorine, antiviral). Safe water storage (e.g., many uses such as the roof top tanks ubiquitous in many parts of the world). Military coatings. |

In the claims, all transitional phrases such as "comprising," "including," "carrying," "having," "containing," "involving," and the like are to be understood to be open-ended, i.e., to mean including but not limited to. Only the transitional phrases "consisting of" and "consisting essentially of," respectively, shall be closed or semi-closed transitional phrases.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES (1) Neely, A. N.; Maley, M. P. *J. Clin. Microbiol.* 2000, 38, 724.
(2) Neely, A. N. *J. Burn. Care. Rehabil.* 2000, 21, 523.
(3) Neely, A. N.; Orloff, M. M. *J. Clin. Microbiol.* 2001, 39, 3360.
(4) Sidwell, R. W.; Dixon, G. J.; McNeil, E. *Appl. Microbiol.* 1966, 14, 55.
(5) Dixon, G. J.; Sidwell, R. W.; McNeil, E. *Appl. Microbiol.* 1966, 14, 183.
(6) Sidwell, R. W.; Dixon, G. J.; McNeil, E. *Appl. Microbiol.* 1967, 15, 921.
(7) Sidwell, R. W.; Dixon, G. J.; Westbrook, L.; Forziati, F. H. *Appl. Microbiol.* 1970, 19, 950.
(8) Sidwell, R. W.; Dixon, G. J.; Westbrook, L.; Forziati, F. H. *Appl. Microbiol.* 1971, 21, 227.
(9) Barker, J.; Vipond, I. B.; Bloomfield, S. F. *J. Hosp. Infect.* 2004, 58, 42.
(10) Dart, B. L.; Obendorf, S. K. *ASTM Special Technical Publication* 2000, STP 1386(7), 251.
(11) Lister, J. *Lancet* 1867, 2, 353.
(12) Oliphant, J. W.; Gordon, D. A.; Meis, A.; Parker, R. R. *Am. J. Hyg.* 1949, 47, 76.
(13) Datta, N.; Pridie, R. B. *J. Hyg. Camb.* 1960, 58, 229.
(14) Standaert, S. M.; Hutcheson, R. H.; Schaffler, W. *Infect. Control Hosp. Epidemiol.* 1994, 15, 22.
(15) Orr, K. E.; Gould, F. K.; Perry, J. D.; Ford, M.; Morgan, S.; Sisson, P. R. *Lancet* 1994, 344, 65.
(16) Phaneuf, M. D.; Ozaki, C. K.; Bide, M. J.; Quist, W. C.; Alessi, J. M.; Tannenbaum, G. A.; LoGerfo, F. W. *J. Biomed. Mater. Res.* 1993, 27, 233.
(17) Aggarwal, P.; Phaneuf, M. D.; Bide, M. J.; Sousa, K. A.; LoGerfo, F. W. *J. Biomed. Mater. Res.* 2005, 75A, 224.
(18) Cen, L.; Neoh, K. G.; Kang, E. T. *J. Biomed. Mater. Res.* 2004, 71A, 70.
(19) Lee, H. J.; Yeo, S. Y.; Jeong, S. H. *J. Mater. Sci.* 2003, 38, 2199.
(20) Braun, M.; Sun, Y. *J. Polym. Sci. Part A Polym. Chem.* 2004, 42, 3818.
(21) Sun, Y.; Sun, G. *J. Appl. Polym. Sci.* 2002, 84, 1592.
(22) Sun, Y.; Chen, T.; Worley, S. D.; Sun, G. *J. Polym. Sci. Part A Polym. Chem.* 2001, 39, 3073.
(23) Sun, Y.; Sun, G. *Ind. Eng. Chem. Res.* 2004, 43, 5015.
(24) Sun, G.; Xu, X. *Textile Chem. Color.* 1998, 30, 26.
(25) Sun, G.; Xu, X.; Bickert, J. R.; Williams, J. F. *Ind. Eng. Chem. Res.* 2001, 40, 1016.
(26) Lin, J.; Winkelman, C.; Worley, S. D.; Broughton, R. M.; Williams, J. F. *J. Appl. Polym. Sci.* 2001, 81, 943.
(27) Bamford, C. H.; Al-Lamee, K. G. *Polymer* 1994, 35, 2844.
(28) Richmond J. Y.; McKinney, R. W. *Biosafety in Microbiological and Biomedical Laboratories*, 4th ed.; U.S. Government printing office: Washington, D.C., 1999.
(29) Haas, H. C.; MacDonald, R. L. *J. Polym. Sci. Part A Polym. Chem.* 1971, 9, 3583.
(30) Hardy, F. E.; Robson, P. *J. Chem. Soc. B.* 1967, 1151.
(31) Zabicky, J. *The Chemistry of Amides*. Interscience: New York, 1970.
(32) March, J. *Advanced Organic Chemistry, Reactions, Mechanisms, and Structure.* $4^{th}$ edition. John Wiley and Sons: New York, 1992.
(33) Robert, S.; Adele, L.; Donald, E. D. *Anal. Chem.* 1964, 36, 636.
(34) George, B. K.; Rajasekharan Pillai V. N. *Macromolecules* 1988, 21, 1867.
(35) Chen, Z. B.; Sun, Y. *Macromolecules* 2005, 38, 8116.
(36) Bloomfield, S. F.; Arthur, M. *Lett. Appl. Microbiol.* 1989, 8, 101.
(37) Larson, M. A.; Marinas, B. J. *Water Res.* 2003, 37, 833.
(38) Sykes, G. *J. Appl. Bact.* 1970, 33, 147.
(39) Tennen, R.; Setlow, B.; Davis, K. L.; Loshon, C. A.; Setlow, P. *J. Appl. Microbiol.* 2000, 89, 330.

What is claimed is:

1. A rechargeable aliphatic N-halamine polymer comprising:
   a cotton substrate;
   a rechargeable aliphatic N-halamine polymer grafted directly to the cotton substrate, wherein the rechargeable aliphatic N-halamine polymer is formed from the polymerization of one or more aliphatic N-halamine methacrylamide monomers selected from N-alkyl-monosubstituted, N-alkylamino-monosubstituted, and N,N-dialkyl-substituted, N,N-dialkylamino-disubstituted; and one or more halides associated with the one or more aliphatic N-halamine methacrylamide monomers, whereby the one or more halides provide inactivation of bacteria cells, spores, fungus, yeasts, viruses or a combination thereof.

2. The composition of claim 1, wherein the rechargeable aliphatic N-halamine polymer is a random polymer, a segmented polymer, a block polymer, a multiblock polymer, a gradient polymer, a graft polymer, a star polymer, a branched polymer, a hyperbranched polymer or segments and combinations thereof.

3. The composition of claim 1, further comprising one or more second aliphatic N-halamine monomer copolymerized with the one or more aliphatic N-halamine methacrylamide monomers to form a random polymer, a segmented polymer, a block polymer, a multiblock polymer, a gradient polymer, a graft polymer, a star polymer, a branched polymer, a hyperbranched polymer or segments and combinations thereof, wherein the one or more second aliphatic N-halamine monomer are selected from an acrylic acid, a methacrylic acid, an ethylacrylic acid, a methyl acrylate, an ethyl acrylate, a propyl acrylate, an n-butyl acrylate, an isobutyl acrylate, an t-butyl acrylate, an 2-ethylhexyl acrylate, a decyl acrylate, a methyl methacrylate, an ethyl methacrylate, a propyl methacrylate, an n-butyl methacrylate isobutyl methacrylate, an t-butyl methacrylate, an 2-ethylhexyl methacrylate, a decyl methacrylate, and combinations thereof in the form of a random polymer, a segmented polymer, a block polymer, a multiblock polymer, a gradient polymer, a graft polymer, a star polymer, a branched polymer, a hyperbranched polymer or segments and combinations thereof.

4. The composition of claim 1, further comprising forming the cotton into a fabric.

5. The composition of claim 1, further comprising a halide source to recharge microbial activity.

6. A rechargeable biocidal organic polymer made by the process comprising the steps:
   polymerizing one or more acyclic N-halamine methacrylamide monomers selected from N-alkyl-monosubstituted, N-alkylamino-monosubstituted, and N,N-dialkyl-substituted, N,N-dialkylamino-disubstituted;
   grafting the rechargeable biocidal organic polymer directly to a cotton; and
   contacting the one or more acyclic N-halamine methacrylamide monomers with a halide source to form an activated acyclic N-halamine organic polymer with biocidal activity against bacteria, spores, fungi, yeasts, virus or a combination thereof.

7. A rechargeable biocidal fabric made by the process comprising the steps:
   forming an acyclic N-halamine methacrylamide polymer from one or more methacrylamide monomers having an acyclic N-halamine compound selected from N-alkyl-monosubstituted, N-alkylamino-monosubstituted, and N,N-dialkyl-substituted, N,N-dialkylamino-disubstituted;
   forming an acyclic N-halamine fabric from the acyclic N-halamine methacrylamide polymer, wherein one or more articles or garments can be constructed from the acyclic N-halamine fabric; and
   contacting the acyclic N-halamine fabric with a halide source to activate the biocidal activity against bacteria, spores, fungi, yeasts, virus or a combination thereof.

8. A method of making an biocidal methacrylamide polymer comprising the steps of:
   polymerizing an acyclic N-halamine methacrylamide monomer selected from N-alkyl-monosubstituted, N-alkylamino-monosubstituted, and N,N-dialkyl-substituted, N,N-dialkylamino-disubstituted into an acyclic N-halamine methacrylamide polymer;
   grafting the rechargeable biocidal organic polymer directly to a cotton; and
contacting the acyclic N-halamine methacrylamide polymer with a halide source to form an activated acyclic N-halamine methacrylamide polymer with biocidal activity against bacteria, spores, fungi, yeasts, virus or a combination thereof.

9. The method of claim 8, wherein the acyclic N-halamine methacrylamide polymer is a random polymer, a segmented polymer, a block polymer, a multiblock polymer, a gradient polymer, a graft polymer, a star polymer, a branched polymer, a hyperbranched polymer or segments and combinations thereof.

10. The method of claim 8, wherein the acyclic N-halamine acrylamide monomer is further modified by the addition of one or more alkyl groups, alkylene groups, alkenyl groups, alkynyl groups, aryl groups, alkoxy groups, alkylcarbonyl groups, alkylcarboxyl groups, amido groups, carboxyl groups, halogens, hydrogens or combinations thereof.

11. The method of claim 8, further comprising the step of forming the cotton into a fabric garment to have biocidal activity against bacteria, spores, fungi, yeasts, virus or a combination thereof.

12. The method of claim 8, further comprising the step of removing one or more halides from the activated acyclic N-halamine methacrylamide polymer and incubating the activated acyclic N-halamine methacrylamide polymer with a halide source to recharged the acyclic N-halamine methacrylamide monomer.

13. The method of claim 8, further comprising a halogenation regenerating step of renewing any removed halogens associated with the acyclic N-halamine methacrylamide monomer with a hypochlorite solution.

* * * * *